United States Patent
Plavina et al.

(10) Patent No.: US 9,726,672 B2
(45) Date of Patent: *Aug. 8, 2017

(54) ANTI-VLA-4 RELATED ASSAYS

(71) Applicant: Biogen MA Inc., Cambridge, MA (US)

(72) Inventors: Tatiana Plavina, North Reading, MA (US); Paula S. Hochman, Newton, MA (US); Michaela Lerner, West Roxbury, MA (US)

(73) Assignee: Biogen MA Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/166,514

(22) Filed: May 27, 2016

(65) Prior Publication Data

US 2016/0274125 A1   Sep. 22, 2016

Related U.S. Application Data

(62) Division of application No. 13/501,111, filed as application No. PCT/US2010/052172 on Oct. 11, 2010, now Pat. No. 9,377,458.

(60) Provisional application No. 61/250,553, filed on Oct. 11, 2009.

(51) Int. Cl.
*G01N 33/68* (2006.01)
*G01N 33/566* (2006.01)
*G01N 33/94* (2006.01)

(52) U.S. Cl.
CPC ....... *G01N 33/6854* (2013.01); *G01N 33/566* (2013.01); *G01N 33/94* (2013.01); *G01N 2333/7055* (2013.01); *G01N 2333/70546* (2013.01); *G01N 2800/26* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 3,817,837 A | 6/1974 | Rubenstein et al. | |
| 3,850,752 A | 11/1974 | Schuurs et al. | |
| 3,996,345 A | 12/1976 | Ullman et al. | |
| 4,235,601 A | 11/1980 | Deutsch et al. | |
| 4,275,149 A | 6/1981 | Litman et al. | |
| 4,277,437 A | 7/1981 | Maggio | |
| 4,366,241 A | 12/1982 | Tom et al. | |
| 4,376,110 A | 3/1983 | David et al. | |
| 4,391,904 A | 7/1983 | Litman et al. | |
| 4,517,288 A | 5/1985 | Giegel et al. | |
| 4,703,017 A | 10/1987 | Campbell et al. | |
| 4,818,677 A | 4/1989 | Hay-Kaufman et al. | |
| 4,837,168 A | 6/1989 | de Jaeger et al. | |
| 4,943,522 A | 7/1990 | Eisinger et al. | |
| 5,096,837 A | 3/1992 | Fan et al. | |
| 5,118,428 A | 6/1992 | Sand et al. | |
| 5,118,630 A | 6/1992 | Glaze | |
| 5,221,616 A | 6/1993 | Kolb et al. | |
| 5,223,220 A | 6/1993 | Fan et al. | |
| 5,225,328 A | 7/1993 | Chang | |
| 5,329,459 A | 7/1994 | Kaufman et al. | |
| 5,415,994 A | 5/1995 | Imrich et al. | |
| 5,434,057 A | 7/1995 | Dorian | |
| 5,521,102 A | 5/1996 | Boehringer et al. | |
| 5,536,646 A | 7/1996 | Sand et al. | |
| 5,541,069 A | 7/1996 | Mortensen et al. | |
| 5,559,041 A | 9/1996 | Kang et al. | |
| 5,686,315 A | 11/1997 | Pronovost et al. | |
| 5,712,172 A | 1/1998 | Huang et al. | |
| 5,763,262 A | 6/1998 | Wong et al. | |
| 5,766,961 A | 6/1998 | Pawlak et al. | |
| 5,770,460 A | 6/1998 | Pawlak et al. | |
| 5,773,234 A | 6/1998 | Pronovost et al. | |
| 5,786,220 A | 7/1998 | Pronovost et al. | |
| 5,804,452 A | 9/1998 | Pronovost et al. | |
| 5,814,455 A | 9/1998 | Pronovost et al. | |
| 5,845,255 A | 12/1998 | Mayaud | |
| 5,939,331 A | 8/1999 | Burd et al. | |
| 6,014,631 A | 1/2000 | Teagarden et al. | |
| 6,187,598 B1 | 2/2001 | May et al. | |
| 6,238,859 B1 | 5/2001 | Luke et al. | |
| 6,305,377 B1 | 10/2001 | Portwood et al. | |

(Continued)

FOREIGN PATENT DOCUMENTS

| | | |
|---|---|---|
| EP | 1712913 A1 | 10/2006 |
| EP | 1933140 A1 | 6/2008 |
| JP | 2005214670 A | 8/2005 |
| JP | 2007197441 A | 8/2007 |
| JP | 08507680 A | 3/2008 |
| JP | 2009-528359 A | 8/2009 |
| JP | 2009531304 A | 9/2009 |
| WO | 94/16094 A2 | 7/1994 |
| WO | 97/19174 A1 | 5/1997 |
| WO | 2004-001539 A2 | 12/2003 |
| WO | 2007100763 A2 | 9/2007 |
| WO | 2011085369 A1 | 7/2011 |
| WO | 2012166971 A2 | 12/2012 |

OTHER PUBLICATIONS

Abbing et al., "Efficient Intracellular Delivery of a Protein and a Low Molecular Weight Substance via Recombinant Polyomavirus-like Particles", The Journal of Biological Chemistry, vol. 279, No. 25, pp. 27410-27421, (2004).

(Continued)

*Primary Examiner* — Jacob Cheu
(74) *Attorney, Agent, or Firm* — Lando & Anastasi, LLP

(57) ABSTRACT

Methods and apparatus for assaying the level of analytes in a sample, related to VLA-4, are disclosed. A method of decreasing the level of an anti-integrin antibody in a subject is described including a) contacting a biological sample from a subject with a detectable capture agent associated with a substrate, wherein the capture agent can bind an anti-integrin antibody in the sample; b) detecting binding of the capture agent with the level of the anti-integrin antibody; and c) treating the subject with plasma exchange until the level of the anti-integrin antibody in the sample reaches a predetermined level.

46 Claims, 4 Drawing Sheets

(56) References Cited

U.S. PATENT DOCUMENTS

| | | | |
|---|---|---|---|
| 6,306,642 B1 | 10/2001 | Nelson et al. | |
| 6,352,862 B1 | 3/2002 | Davis et al. | |
| 6,485,982 B1 | 11/2002 | Charlton | |
| 6,534,320 B2 | 3/2003 | Ching et al. | |
| 6,620,626 B1 | 9/2003 | Bodily | |
| 6,623,981 B2 | 9/2003 | Billheimer et al. | |
| 6,767,714 B2 | 7/2004 | Nazareth et al. | |
| 6,790,611 B2 | 9/2004 | Lassen et al. | |
| 7,419,666 B1 | 9/2008 | Iliaki et al. | |
| 7,807,167 B2 | 10/2010 | Taylor et al. | |
| 2001/0021910 A1 | 9/2001 | Goldstein | |
| 2002/0052543 A1 | 5/2002 | Williams et al. | |
| 2003/0032923 A1 | 2/2003 | Eakins et al. | |
| 2004/0248216 A1 | 12/2004 | Seino | |
| 2005/0215869 A1 | 9/2005 | Elsayed et al. | |
| 2005/0283385 A1 | 12/2005 | Hunkeler et al. | |
| 2007/0190667 A1 | 8/2007 | Cole et al. | |
| 2007/0231319 A1 | 10/2007 | Yednock | |
| 2008/0044382 A1 | 2/2008 | Lieberburg | |
| 2008/0233150 A1 | 9/2008 | Smith et al. | |
| 2009/0216107 A1 | 8/2009 | Rubin et al. | |

OTHER PUBLICATIONS

Agostini et al., "JC Virus (JCV) Genotypes in Brain Tissue from Patients with Progressive Multifocal Leukoencephalopathy (PML) and in Urine from Controls without PML: Increased Frequency of JCV Type 2 in PML", Journal of Infectious Diseases, vol. 176, No. 1, p. 6, (1997).
Bloomgren et al., "Risk of Natalizumab-Associated Progressive Multifocal Leukoencephalopathy", The New England Journal of Medicine, vol. 366, p. 1874, (2012).
Bozic et al., "Anti-John Cunningham virus antibody prevalence in multiple sclerosis patients: baseline results of Stratify-1." Ann Neurol. http://www.nbci.nlm.nih.gov/pubmed/22162056>Nov. 2011; 70(5):742-50. doi: 10.1002/ana.22606.
Braun et al., Oligonucleotide and plasmid DNA packaging into polyoma VP1 virus-like particles expressed in *Escherichia coli* Biotechnol. Appl. Biochem. (1999) 29, 31-43.
Calabresi et al., "The incidence and significance of anti-natalizumab antibodies: results from Affirm and Sentinel", Neurology, vol. 69,Nr:14,pp. 1391-1403.
Casal J I: "Use of the baculovirus expression system for the generation of virus-like particles.", Biotechnology & Genetic Engineering Reviews 2001, vol. 18, 2001, pp. 73-87.
Chang et al: "Self-assembly of the JC virus major capsid protein, VP1, expressed in insect cells", Journal of General Virology (1997), vol. 78, pp. 1435-1439.
Egli et al., "Prevalence of polyomavirus BK and JC infection and replication in 400 healthy blood donors", J. Infect Dis. 199:837-846, 2009.
EP Search Report for EP 07 81 3941 dated Mar. 21, 2013.
Extended European Search Report for EP 10 82 2820 dated Apr. 4, 2013.
Goelz Ph.D , "Assay design and sample collection can affect anti-John Cunningham virus antibody detection" Annals of Neurology, vol. 69, Issue 2, <http://onlinelibrary.wiley.com/doi/10.1002/ana.v69.2/issuetoc>pp. 429-430, Feb. 2011.
Goldman, et al., "Molecular cloning and expression of major structural protein VP1 of the human polyomavirus JC virus: formation of virus-like particles useful for immunological and therapeutic studies" Journal of Virology, vol. 73, No. 5, pp. 4465-4469, 1999.
Gorelik et al., "Anti-JC Virus Antibodies: Implications for PML Risk Stratification", Ann Neurol, vol. 68, No. 3, p. 295-303, (2010).
International Preliminary Report on Patentability for PCT/US2007/075577 dated Feb. 10, 2009.
International Preliminary Report on Patentability for PCT/US2011/020832 dated Jul. 17, 2012.
International Search Report and Written Opinion for Application No. PCTUS1439525 dated Oct. 20, 2014.
International Search Report and Written Opinion for PCT/US12/40283 dated Dec. 17, 2012.
International Search Report for PCT/US10/52172 dated Dec. 14, 2010.
International search report for PCT/US2007/075577 dated Oct. 30, 2008.
International Search Report for PCT/US2011/020832 dated Mar. 14, 2011.
Jilek at al.: "Immune responses to JC virus in patients with multiple sclerosis treated with natalizumab: a cross-sectional and longitudinal study", Lancet Neurology (published online Jan. 29, 2010), vol. 9, Mar. 2010, pp. 264-272.
Khatri et al., "Plasma Exchange Accelerates the Decline of Serum Natalizumab Concentration in Patients with Multiple Sclerosis: Results of the Natalizumab PLEX Study", Neurology, 70, pp. A227-A228, (2008).
Khatri et al., "Plasma Exchange Accelerates the Decline of Serum Natalizumab Concentration in Patients with Multiple Sclerosis: Results of the Natalizumab PLEX Study", Presentation, (2008).
Khatri, et al., "Effect of plasma exchange in accelerating natalizumab clearance and restoring leukocyte function", Neurology vol. 72. No. 5, (Feb. 3, 2009). p. 402-409.
Khatri, et al., 60th Annual Meeting of American Academy of Neurology, Chicago, Apr. 2008.
Knowles W A et al: "The JC virus antibody response in serum and cerebrospinal fluid in progressive multifocal leucoencephalopathy.", Clinical and Diagnostic Virology vol. 4, No. 2, Aug. 1995, pp. 183-194.
Koren, Smith E, et al., "Recommendations on risk-based strategies for detection and characterization of antibodies against biotechnology products" Journal of Immunological Methods, vol. 333,Nr:1-2,pp. 1-9, 2008 publication year.
Major, "Progressive Multifocal Leukoencephalopathy in Patients on Immunomodulatory Therapies", Annu. Rev. Med. 61:35-47 (2010), Aug. 31, 2009, Epub ahead of print.
Miller D H: "Colloquium C15: Natalizumab (anti-VLA4 antibody) in multiple sclerosis", Journal of Neurochemistry, Wiley Interscience, New York, NY, US, vol. 85, No. Suppl. 1, Jan. 1, 2003, p. 96, C15-04, XP003009634, ISSN: 0022-3042.
Millipore, "Short Guide for Developing Immunochromatographic Test Strip", (1996).
Montross et al.: "Nuclear Assembly of Polyomavirus Capsids in Insect Cells Expressing the Major Capsid Protein VP1", Journal of Virology (Sep. 1991), vol. 65, No. 9, pp. 4991-4998.
Ou et al.: "The major capsid protein, VP1, of human JC virus expressed in *Escherichia coli* is able to self-assemble into a capsid-like particle and deliver exogenous DNA into human kidney cells", Journal of General Virology (1999), vol. 80, pp. 39-46.
Padgett et al., "Prevalence of antibodies in human sera against JC virus, an isolate from a case of progressive multifocal leukoencephalopathy", J. Infect. Dis. 127:467-70, 1973.
Piccinni, et al., "Stronger association of drug-induced progressive multifocal leukoencephalopathy (PML) with biological immunomodulating agents", Eur. J. Clin. Pharmacol. 66:199-206, 2010.
Plavina et al: "Anti-JCV antibody index further defines PML risk in natalizumab-treated MS patients", The 27th Annual Meeting of the Corsortium of Multiple Sclerosis Centers Acknowledgements, Accessed March Neurology. Neurology, Wamke C J Neurol Neurosurg Psychiatry Ann Neurol, May 30, 2013 (May 30, 2013), pp. 1736-1742.
Preliminary Report on Patentability for PCT/US10/52172 dated Apr. 11, 2012.
Rollison Dana E et al: "Prediagnostic circulating antibodies to JC and BK human polyomaviruses and risk of non-Hodgkin lymphoma.", Cancer Epidemiology, Biomarkers & Prevention : A Publication of the American Association for Cancer Research, Cosponsored by the American Society of Preventive Oncology Mar. 2006, vol. 15, No. 3, Mar. 2006 (Mar. 2006), pp. 543-550.
Salunke et al., "Polymorphism in the Assembly of Polyomavirus Capsid Protein VP", Biophys Journal, vol. 56, pp. 387-900, (1989).

(56) References Cited

OTHER PUBLICATIONS

Sandrock et al.: "Risk Stratification for Progressive Multifocal Leukoencephalopathy (PML) in MS Patients: Role of Prior Immunosuppressant Use, Natalizumab-Treatment Duration, and Anti-JCV Antibody Status", Neurology, vol. 76, No. 9, Suppl. 4, Mar. 2011 (Mar. 2011), p. A248, 63rd Annual Meeting of the American Academy of Neurology; Honolulu, HI, USA; Apr. 9-16, 2011.
Sandrock, et al., "Risk of Natalizumab-Associated Progressive Multifocal Leukoencephalopathy" 25th Annual Meeting of the Consortium of Multiple Sclerosis Centers, Jun. 1-4, 2011 Montreal, Quebec, Canada.
Stolt et al.: "Seroepidemiology of the human polyomaviruses", Journal of General Virology (2003), vol. 84, pp. 1499-1504.
Stuve, et al., "Potential Risk of Progressive Multifocal Leukoencephalopathy With Natalizumab Therapy", Arch Neurol. vol. 64, (Feb. 2007). pp. 169-176.
Subramanyam et al.: "Anti-JCV Antibodies Are Consistently Detected Prior to and after PML Diagnosis in Natalizumab-Treated MS Patients", Neurology, vol. 76, No. 9, Suppl. 4, Mar. 2011 (Mar. 2011), pp. A636-A637, 63rd Annual Meeting of the American Academy of Neurology; Honolulu, HI, USA; Apr. 9-16, 2011.
Supplementary European Search Report dated Aug. 30, 2013 for EP 11 73 2315.
Supplementary Partial European Search Report from corresponding European Application No. 12792375.3 dated Jun. 1, 2015.
Takada, et al., "The integrins", Genome Biol. 8:215 (2007).
Third Party Observation for European Application No. EP 11732315.4 dated Jun. 9, 2015.
Third Party Observation for European Patent Application No. 11732315.4 dated Dec. 10, 2014.
Van Assche, "Progressive Multifocal Leukoencephalopathy After Natalizumab Therapy for Crohn's Disease", The New England Journal of Medicine, vol. 353, No. 4, pp. 362-368, (2005).
Verbeeck J et al: "JC viral loads in patients with Crohn's disease treated with immunosuppression: can we screen for elevated risk of progressive multifocal leukoencephalopathy?", GUT vol. 57, No. 10, Oct. 2008.
Viscidi, "Serological Cross-Reactivities between Antibodies to Simian Virus 40, BK Virus, and JC Virus Assessed by Virus-Like-Particle-Based Enzyme Immunoassays", Clinical and Diagnostic Laboratory Immunology, vol. 10, No. 2, pp. 278-285, (2003).
Warnke et al: "Natalizumab and progressive multifocal leukoencephalopathy: what are the causal factors and can it be avoided?", Archives of Neurology, vol. 67, No. 8, Aug. 1, 2010 (Aug. 1, 2010), pp. 923-930.
Weber T et al: "Analysis of the systemic and intrathecal humoral immune response in progressive multifocal leukoencephalopathy.", The Journal of Infectious Diseases vol. 176, No. 1, Jul. 1997 pp. 250-254.
Wenning, et al., Treatment of Progressive Multifocal Leukoencephalopathy Associated with Natalizumab, N Engl J Med, vol. 361. No. 11. (Sep. 10, 2009), p. 1075-1080.
Wikipedia, "Polyomavirus Capsid Protein (VP1)", Retrieved from the Internet: URL: http://en.wikipedia.org/wiki/Polyomavirus_capsid_protein_(VP1), (2015).
Written Opinion for PCT/US10/52172 dated Dec. 14, 2010.
Written Opinion for PCT/US2007/075577 dated Feb. 9, 2009.
Written Opinion for PCT/US2011/020832 dated Mar. 14, 2011.
Trampe, A. K., et al. "Anti-JC virus antibodies in a large German natalizumab-treated multiple sclerosis cohort." Neurology 78.22 (2012): 1736-1742.

ANTI-VLA-4 RELATED ASSAYS

CLAIM OF PRIORITY

This application is a Divisional of U.S. patent application Ser. No. 13/501,111, filed on Jun. 27, 2012, which is a national phase application under 35 U.S.C. §371 of PCT International Application No. PCT/US2010/052172, filed on Oct. 11, 2010, which claims priority to U.S. Provisional Patent Application No. 61/250,553, filed on Oct. 11, 2009. The contents of the aforesaid applications are hereby incorporated by reference in their entirety.

FIELD OF THE INVENTION

The invention relates to assays associated with immunomodulatory therapies

SUMMARY OF THE INVENTION

The invention is based, at least in part, on the development of a test to assay the level of an anti-integrin antibody and the anti-(anti-integrin antibody) antibody, e.g., anti-drug antibody, in a sample.

In one aspect, a method of decreasing the level of an anti-integrin antibody in a subject includes contacting a biological sample from a subject with a detectable capture agent associated with a substrate, wherein the capture agent can bind an anti-integrin antibody in the sample, detecting binding of the capture agent with a level of the anti-integrin antibody in the sample, and treating the subject with plasma exchange until the level of the anti-integrin antibody in the sample reaches a predetermined level. The method can include a subject who was treated with a natalizumab and has been diagnosed with or is suspected of having a JC virus infection.

Certain embodiments can include one or more of the following features. Contacting the biological sample with a detectable capture agent and detecting binding of the capture agent can include assaying in a lateral flow system. The binding of the capture agent with the antibody in the sample can produce a detectable signal. Binding of the capture agent with the antibody can be detected by a secondary agent. The predetermined level of the antibody can be about 1 µg/ml, 2 µg/ml, 3 µg/ml, 4 µg/ml, 5 µg/ml, 6 µg/ml, 7 µg/ml, 8 µg/ml, 9 µg/ml, 10 µg/ml, 15 µg/ml, or 20 µg/ml. Contacting a biological sample from a subject with a detectable capture agent associated with a substrate, and detecting binding of the capture agent to the antibody can occur one day, two days, three days, four days, five days, six days, one week, two weeks, three weeks, or four weeks after the plasma exchange treatment. The plasma exchange treatment can be repeated once a day, or once every two days, three days, four days, five days, six days, one week, two weeks, three weeks, or four weeks. The biological sample can be blood, plasma, serum, urine, saliva, cerebrospinal fluid, sputum, ocular lens fluid, sweat, milk, ascites fluid, mucous, synovial fluid, peritoneal fluid, transdermal exudates, pharyngeal exudates, bronchoalveolar lavage, tracheal aspirations, semen, cervical mucus, vaginal secretion, urethral secretion, or amniotic fluid. The anti-integrin antibody can be a recombinant anti-integrin antibody or an anti-alpha4 integrin chain antibody. The capture agent can be an antibody or an integrin.

In another aspect, an apparatus for assaying the level of an anti-integrin antibody in a biological sample includes a substrate, and a detectable capture agent associated with the substrate, wherein the capture agent can bind an anti-integrin antibody in the biological sample.

Certain embodiments can include one or more of the following features. The apparatus can include a lateral flow system. The binding of the capture agent to the anti-integrin antibody can produce a detectable signal. The binding of the capture agent to the anti-integrin antibody can be detected by a secondary agent. The capture agent can be an antibody or an integrin. The anti-integrin antibody can be a recombinant anti-integrin antibody. The recombinant anti-integrin antibody is an anti-alpha4 integrin chain antibody. The substrate can be nitrocellulose, cellulose acetate, filter paper, cloth, or glass fiber paper. The biological sample can be blood, plasma, serum, urine, saliva, cerebrospinal fluid, sputum, ocular lens fluid, sweat, milk, ascites fluid, mucous, synovial fluid, peritoneal fluid, transdermal exudates, pharyngeal exudates, bronchoalveolar lavage, tracheal aspirations, semen, cervical mucus, vaginal secretion, urethral secretion, or amniotic fluid. The binding of the capture agent to the antibody can be detectable within about 30 seconds to about 60 minutes or longer after the binding.

In another aspect, a method of assaying the level of an anti-integrin antibody in a biological sample includes obtaining a biological sample from a subject, contacting the sample with a detectable capture agent associated with a substrate, wherein the capture agent can bind an anti-integrin antibody in the sample, and detecting and correlating binding of the capture agent to the level of the anti-integrin antibody. The method can include a subject who was treated with a natalizumab and has been diagnosed with or is suspected of having a JC virus infection.

Certain embodiments can include one or more of the following features. Contacting the sample with a detectable capture agent and detecting the binding of the capture agent can include assaying in a lateral flow system. The binding of the capture agent to the antibody can produce a detectable signal. Binding of the capture agent to the antibody can be detected by a secondary agent. The method can include administering a treatment to the subject to decrease the level of the anti-integrin antibody in the subject. The treatment can be plasma exchange. The level of the anti-integrin antibody can be measured one day, two days, three days, four days, five days, six days, one week, two weeks, three weeks, or four weeks after the administration of the treatment. Administering the treatment and measuring the level of the anti-integrin antibody can be repeated until the level of the anti-integrin antibody in the sample reaches a predetermined level. The predetermined level can be about 1 µg/ml, 2 µg/ml, 3 µg/ml, 4 µg/ml, 5 µg/ml, 6 µg/ml, 7 µg/ml, 8 µg/ml, 9 µg/ml, 10 µg/ml, 15 µg/ml, or 20 µg/ml. The treatments can be administered once a day, or once every two days, three days, four days, five days, six days, one week, two weeks, three weeks, or four weeks. The anti-integrin antibody can be a recombinant anti-integrin antibody. The anti-integrin antibody can be an anti-alpha4 integrin chain antibody. The capture agent can be an antibody or an integrin. The biological sample can be blood, plasma, serum, urine, saliva, cerebrospinal fluid, sputum, ocular lens fluid, sweat, milk, ascites fluid, mucous, synovial fluid, peritoneal fluid, transdermal exudates, pharyngeal exudates, bronchoalveolar lavage, tracheal aspirations, semen, cervical mucus, vaginal secretion, urethral secretion, or amniotic fluid.

In another aspect, a method of assaying the efficacy of a treatment can be obtaining a biological sample from a subject undergoing treatment to decrease the level of an anti-integrin antibody in the subject, contacting the sample with a detectable capture agent associated with a substrate, wherein the capture agent can bind an anti-integrin antibody in the sample, and detecting and correlating the binding of the capture agent to the level of the anti-integrin antibody, wherein a level of the anti-integrin antibody in the sample less than a predetermined level is indicative of the efficacy of the treatment. The method can include a subject who was treated with a natalizumab and has been diagnosed with or is suspected of having a JC virus infection.

Certain embodiments can include one or more of the following features. Contacting the sample with a detectable capture agent and detecting and correlating the binding of the capture agent can include assaying in a lateral flow system. The binding of the capture agent to the antibody can produce a detectable signal. Binding of the capture agent to the antibody can be detected by a secondary agent. The predetermined level can be about 1 µg/ml, 2 µg/ml, 3 µg/ml, 4 µg/ml, 5 µg/ml, 6 µg/ml, 7 µg/ml, 8 µg/ml, 9 µg/ml, 10 µg/ml, 15 µg/ml, or 20 µg/ml. The biological sample can be obtained from the subject one day, two days, three days, four days, five days, six days, one week, two weeks, three weeks, or four weeks after the treatment. The treatment can be repeated once a day, or once every two days, three days, four days, five days, six days, one week, two weeks, three weeks, or four weeks. The treatment can include plasma exchange. The biological sample can be blood, plasma, serum, urine, saliva, cerebrospinal fluid, sputum, ocular lens fluid, sweat, milk, ascites fluid, mucous, synovial fluid, peritoneal fluid, transdermal exudates, pharyngeal exudates, bronchoalveolar lavage, tracheal aspirations, semen, cervical mucus, vaginal secretion, urethral secretion, or amniotic fluid. The anti-integrin antibody can be a recombinant anti-integrin antibody. The anti-integrin antibody can be an anti-alpha4 antibody. The capture agent can be an antibody or an integrin.

In another aspect, a kit for assaying the level of an anti-integrin antibody in a biological sample for use in treating with measuring the level of an anti-integrin antibody in a subject and monitoring the efficacy of the treatment includes a tester that includes a substrate and a detectable capture agent associated with the substrate. The capture agent can bind an anti-integrin antibody in the biological sample and a chase buffer. The subject can include a subject who was treated with a natalizumab and has been diagnosed with or is suspected of having a JC virus infection. The kit can further include instructions for interpreting the level of the anti-integrin antibody. The kit can also be used to monitor the efficacy of treatment in the subject.

Certain embodiments of the kit can include one or more of the following features. The substrate can be a portion of a lateral flow system. The binding of the capture agent to the antibody can produce a detectable signal. The binding of the capture agent to the antibody can be detected by a secondary agent. The capture agent can be an antibody or an integrin. The anti-integrin antibody can be a recombinant anti-integrin antibody. The recombinant anti-integrin antibody can be an anti-alpha4 antibody. The substrate can be nitrocellulose, cellulose acetate, filter paper, cloth, or glass fiber paper. The biological sample can be blood, plasma, serum, urine, saliva, cerebrospinal fluid, sputum, ocular lens fluid, sweat, milk, ascites fluid, mucous, synovial fluid, peritoneal fluid, transdermal exudates, pharyngeal exudates, bronchoalveolar lavage, tracheal aspirations, semen, cervical mucus, vaginal secretion, urethral secretion, or amniotic fluid. The binding of the capture agent to the antibody can be detectable within about 30 seconds to about 60 minutes or longer after the binding.

In another aspect, a method of assaying the efficacy of a treatment can be obtaining a biological sample from a subject undergoing treatment with anti-VLA4 antibody, contacting the sample with a detectable capture agent associated with a substrate, wherein the capture agent can bind an anti-anti-integrin antibody in the sample, and detecting and correlating the binding of the capture agent to the level of the anti-anti-integrin antibody to determine the efficacy of the treatment.

Certain embodiments can include one or more of the following features. Contacting the sample with a detectable capture agent and detecting and correlating the binding of the capture agent can include assaying in a lateral flow system. The binding of the capture agent to the antibody can produce a detectable signal. Binding of the capture agent to the antibody can be detected by a secondary agent. The biological sample can be obtained from the subject prior to treatment or one day, two days, three days, four days, five days, six days, one week, two weeks, three weeks, or four weeks after the treatment. Obtaining the biological sample can be repeated once a day, or once every two days, three days, four days, five days, six days, one week, two weeks, three weeks, or four weeks. The biological sample can be blood, plasma, serum, urine, saliva, cerebrospinal fluid, sputum, ocular lens fluid, sweat, milk, ascites fluid, mucous, synovial fluid, peritoneal fluid, transdermal exudates, pharyngeal exudates, bronchoalveolar lavage, tracheal aspirations, semen, cervical mucus, vaginal secretion, urethral secretion, or amniotic fluid. The anti-anti-integrin antibody can be a recombinant anti-anti-integrin antibody. The anti-anti-integrin antibody can be an anti-anti-alpha4 integrin chain antibody. The capture agent can be an antibody.

In another aspect, a kit for assaying the level of an anti-anti-VLA4 antibody in a biological sample and monitoring the efficacy of anti-VLA4 antibody treatment in a subject includes a tester that includes a substrate and a detectable capture agent associated with the substrate, wherein the capture agent can bind an anti-anti-VLA4 antibody in the biological sample and a chase buffer. The kit can further include instructions for interpreting the level of the anti-anti-VLA4 antibody. The kit can also be used to monitor the efficacy of treatment in the subject.

In certain embodiments the kit can include one or more of the following features. The substrate can be a portion of a lateral flow system. The binding of the capture agent to the antibody can produce a detectable signal. The binding of the capture agent to the antibody can be detected by a secondary agent. The capture agent can be an antibody. The substrate can be nitrocellulose, cellulose acetate, filter paper, cloth, or glass fiber paper. The biological sample can be blood, plasma, serum, urine, saliva, cerebrospinal fluid, sputum, ocular lens fluid, sweat, milk, ascites fluid, mucous, synovial fluid, peritoneal fluid, transdermal exudates, pharyngeal exudates, bronchoalveolar lavage, tracheal aspirations, semen, cervical mucus, vaginal secretion, urethral secretion, or amniotic fluid. The binding of the capture agent to the antibody can be detectable within about 30 seconds to about 60 minutes or longer after the binding.

In another aspect, a method of detecting anti-drug antibodies in a biological sample can be obtaining a biological sample from a subject undergoing treatment with anti-VLA4 antibody, contacting the sample with a detectable capture agent associated with a substrate, wherein the capture agent can bind an anti-anti-integrin antibody in the sample, and detecting and correlating the binding of the capture agent to the level of the anti-anti-integrin antibody to determine the efficacy of the treatment.

In another aspect, a kit for detecting anti-anti-VLA4 antibody in a biological sample includes a tester that includes a substrate and a detectable capture agent associated with the substrate, wherein the capture agent can bind an anti-anti-VLA4 antibody in the biological sample and a chase buffer.

DEFINITIONS

The articles "a" and "an" are used herein to refer to one or to more than one (i.e., to at least one) of the grammatical object of the article. By way of example, "an element" means one element or more than one element.

The term "about" is used herein to mean a value ±20% of a given numerical value. Thus, "about 60%" means a value of between 60±(20% of 60) (i.e., between 48 and 70).

The term "or" is used herein to mean, and is used interchangeably with, the term "and/or," unless context clearly indicates otherwise.

As used herein, the term "purify," "purified," or "purification" means the removal or isolation of a molecule from its environment by, for example, isolation or separation. "Substantially purified" molecules are at least about 60% free, for example, at least about 75% free, or at least about 90% free from other components with which they are associated. In some cases, a substantially purified molecule is at least 60% free, 75% free, 90%, or 95% free from other components. As used herein, these terms also refer to the removal of contaminants from a sample.

As used herein, "sample" refers to anything that may contain an analyte for which an analyte assay is desired. The sample may be a biological sample, such as a biological fluid or a biological tissue. Examples of biological fluids include blood, serum, plasma, saliva, sputum, ocular lens fluid, sweat, urine, milk, ascites fluid, mucous, synovial fluid, peritoneal fluid, transdermal exudates, pharyngeal exudates, bronchoalveolar lavage, tracheal aspirations, cerebrospinal fluid, semen, cervical mucus, vaginal or urethral secretions, amniotic fluid or the like. Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s).

As used herein, "fluid sample" refers to a material suspected of containing an analyte(s) of interest, which material has sufficient fluidity to flow through a device or assay described herein. A fluid sample can be obtained from a source and used directly in an assay described herein or can be pretreated so as to modify its character. Such samples can include human, animal or man-made samples. The sample can be prepared in any medium that does not interfere with an assay described herein. Typically, the sample is an aqueous solution or biological fluid described herein.

A fluid sample can be derived from any source, such as a physiological fluid, including blood, serum, plasma, saliva, sputum, ocular lens fluid, sweat, urine, milk, ascites fluid, mucous, synovial fluid, peritoneal fluid, transdermal exudates, pharyngeal exudates, bronchoalveolar lavage, tracheal aspirations, cerebrospinal fluid, semen, cervical mucus, vaginal or urethral secretions, amniotic fluid, and the like. Fluid homogenates of cellular tissues such as, for example, hair, skin and nail scrapings. In addition, a solid material to be assayed for the presence of an analyte can be used as a test sample once it is modified to form a liquid medium, e.g., and extract, or to release the analyte.

As used herein, "antigen" means any compound capable of binding to an antibody, or against which antibodies can be raised.

As used herein, "antibody" refers to a polypeptide substantially encoded by an immunoglobulin gene or immunoglobulin genes, or fragments thereof. Recognized immunoglobulin genes include the kappa, lambda, alpha, gamma, delta, epsilon, and mu constant regions, as well as myriad immunoglobulin variable region genes. Light chains are classified as either kappa or lambda. Heavy chains are classified as gamma, mu, alpha, delta, or epsilon, which in turn define the immunoglobulin classes IgG, IgM, IgA, IgD, and IgE, respectively. Typically, an antibody is an immunoglobulin having an area on its surface or in a cavity that specifically binds to and is thereby defined as complementary with a particular spatial and polar organization of another molecule. The antibody can be polyclonal or monoclonal. Antibodies may include a complete immunoglobulin or fragments thereof. Fragments thereof can include, for example, Fab, Fab', F(ab')$_2$, Fv, single chain Fv (scFv), and the like. Antibodies may also include chimeric antibodies or fragment thereof made by recombinant methods. In some cases the detected antibody is an IgG4 antibody. In an assay as described herein, IgG4 half antibodies are detected, complete IgG4 antibodies are detected, or both IgG4 half antibodies and IgG4 complete antibodies are detected.

As used herein, the term "analyte" refers to a known or unknown component of a sample, which will specifically bind to a capture agent if the analyte and the capture agent are members of a specific binding pair. In general, analytes are biopolymers, e.g., an oligomer or polymer such as an oligonucleotide, a polypeptide, (e.g., an antibody), or the like. In some embodiments, an analyte can exist in a mobile phase (such as in a fluid) to be detected by a capture agent.

As used herein, the term "labeled reagent" refers to a substance comprising a detectable label attached to a specific binding agent. The attachment may be covalent or non-covalent binding, but the method of attachment is not critical. The label allows the labeled reagent to produce a detectable signal that is related to the presence of an analyte in a sample described herein. The specific binding agent component of the labeled reagent is selected to directly or indirectly bind to an analyte. The labeled reagent can be associated with a substrate described herein, it can be combined with a fluid sample to form a fluid solution, it can be added to a substrate separately from a sample, or it can be predeposited or reversibly immobilized on the substrate. In addition, the specific binding agent may be labeled before or during the performance of an assay described herein by means of any suitable attachment method known in the art. The detectable label can be a directly detectable label or a label that is detected using indirect methods.

As used herein, the term "detectable signal" refers to a signal produced by the binding of a capture agent with an analyte. In some embodiments, a detectable signal is detectable by visual inspection. Without limitation, the type of signal produced depends on the label used. Generally, detectable signals indicating the presence or absence of an analyte in a sample may be evident of their own accord, e.g., detectable as lines, plus or minus signs, or particularly shaped symbols, or may be evident through comparison with a reference, such as a color indicator reference.

As used herein, the term "capture agent" refers to an agent that binds an analyte through an interaction that is sufficient to permit the agent to specifically bind an analyte. For example, the capture agent can specifically bind an analyte with a dissociation constant ($K_d$) of less than about $10^{-6}$ M without binding to other targets. The binding interaction can be mediated by a binding site of the capture agent. Capture agents can include, e.g., any polypeptide, e.g., an antibody. Capture agents can be bound to a substrate or can be present in solution.

As used herein, the term "specific binding" refers to preferential binding of an agent to a particular analyte that is present in a mixture of different analytes. Typically, specific binding differentiates between a desirable and undesirable analytes in a sample. A specific binding agent typically differentiates between a desirable and undesirable analyte by binding more than about 10 to 100-fold or more to a desirable analyte in preference to other analytes. In certain circumstances, such preferential binding can be at least 1000- to 10,000-fold. For example, the affinity between a capture agent and analyte when they are specifically bound in a capture agent/analyte complex is at least about $10^{-7}$ M, at least about $10^{-8}$ M, at least about $10^{-9}$ M, at least about $10^{-10}$ M, or about at least $10^{-11}$ e.g., at least $10^{-7}$ M, at least $10^{-8}$ M, at least $10^{-9}$ M, at least $10^{-10}$ M, or at least $10^{-11}$.

As used herein, the term "capture agent/analyte complex" is a complex that results from the specific binding of a capture agent with an analyte.

As used herein, "binding partners" refers to pairs of molecules that can be found in a capture agent/analyte complex, i.e., exhibit specific binding with each other.

As used herein, the term "assessing" refers to any form of measurement, and includes determining if an element is present or not. The terms "determining", "measuring", "evaluating", "assessing", and "assaying" are used interchangeably and include both quantitative and qualitative determinations.

As used herein, a "detectable label" refers to an atom (e.g., radionuclide), molecule (e.g., fluorescein), or complex, that is detected or can be used to detect (e.g., due to a physical or chemical property) the presence of an analyte, or to enable binding of another molecule to which it is covalently bound or otherwise associated. The term also refers to covalently bound or otherwise associated molecules (e.g., a biomolecule such as an enzyme) that act on a substrate to produce a detectable atom, molecule or complex. Detectable labels include any composition detectable by spectroscopic, photochemical, biochemical, immunochemical, electrical, optical or chemical means. For example, labels include biotin for staining with labeled streptavidin conjugate, magnetic beads (e.g., Dynabeads™.), fluorescent dyes (e.g., fluorescein, Texas red, rhodamine, green fluorescent protein, enhanced green fluorescent protein, and the like), radiolabels (e.g., $^3$H, $^{125}$I, $^{35}$S, $^{14}$C, or $^{32}$P), enzymes (e.g., hydrolases, particularly phosphatases such as alkaline phosphatase, esterases and glycosidases, or oxidoreductases, particularly peroxidases such as horse radish peroxidase, and others commonly used in ELISAs), substrates, cofactors, inhibitors, chemiluminescent groups, chromogenic agents, and colorimetric labels such as colloidal metallic particles (such as gold), colloidal non-metallic particles (such as selenium or tellurium), or colored glass or plastic (e.g., polystyrene, polypropylene, latex, etc.) beads. Non-limiting examples of patents disclosing such labels include U.S. Pat. Nos. 3,817,837; 3,850,752; 3,939,350; 3,996,345; 4,277,437; 4,275,149; and 4,366,241, each of which is incorporated by reference in its entirety. Means of detecting such labels are known to those of skill in the art.

As used herein, the terms "sandwich", "sandwich ELISA", "sandwich diagnostic", and "capture ELISA" refer to the concept of detecting an analyte with two or more different test agents. For example, a capture agent can be directly or indirectly attached to a substrate, and a test sample can be passed over the surface of the substrate allowing the capture agent to specifically bind its cognate analyte. A labeled reagent, e.g., a labeled antibody or alternative detection reagent (which can bind the analyte), can then be used to determine whether a capture agent specifically bound the analyte.

As used herein, the term "substrate" means any support capable of binding or being associated with a capture agent. Well-known substrates include glass, polystyrene, polypropylene, polyethylene, dextran, nylon, amylases, natural and modified celluloses, polyacrylamides, agarose, and magnetite. The nature of the substrate can be either soluble to some extent or insoluble. The structure of the substrate is not limiting, and the substrate can have any structural configuration so long as the capture agent is capable of binding to an analyte. Thus, the structural configuration can be spherical, as in a bead, or cylindrical, as in the inside surface of a test tube, or the external surface of a rod. Alternatively, the surface can be flat, such as a sheet, culture dish, test strip, etc. Those skilled in the art will know many other suitable substrates for binding or being associated with a capture agent, or can ascertain the same by routine experimentation.

As used herein, the term "subject" refers to any animal, e.g., a mammal, human or non-human. Exemplary subjects include, but are not limited to, humans, non-human primates, mice, rats, guinea pigs, cattle, sheep, goats, pigs, dogs, cats, birds, deer, elk, rabbit, reindeer, deer, and horses.

As used herein, the term "measuring the level of" refers to detection both quantitatively and qualitatively.

The following figures are presented for the purpose of illustration only, and are not intended to be limiting.

Figure 1:
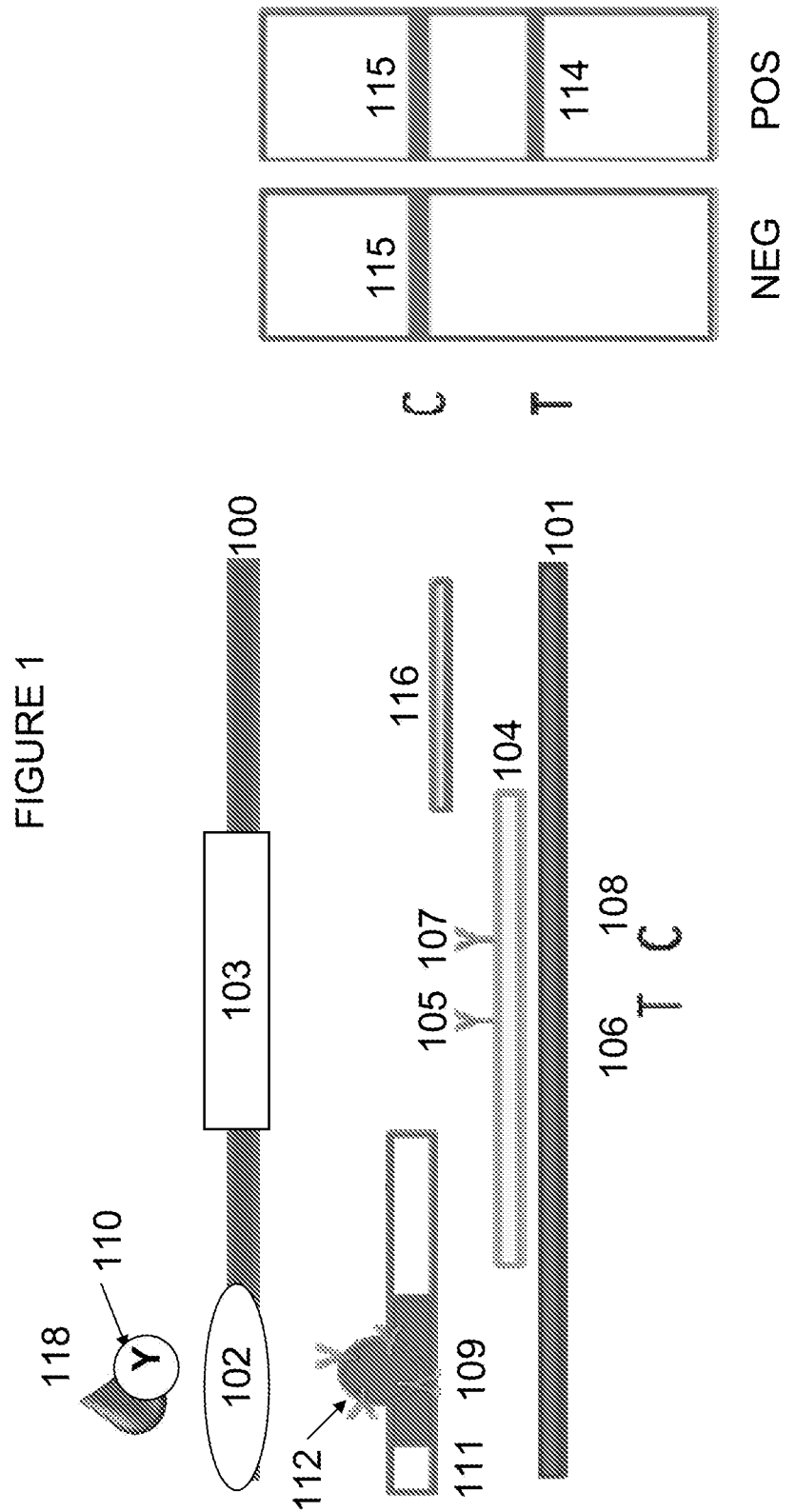
FIG. 1 is a schematic of the lateral flow apparatus and the results of a test corresponding to Example 1 following the loading of various components.

Other features and advantages of the invention will be apparent from the following detailed description, and from the claims.

DETAILED DESCRIPTION

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein, including GenBank database sequences, are incorporated by reference in their entirety. In case of conflict, the present specification, including definitions, will control. In addition, the materials, methods, and examples are illustrative only and not intended to be limiting.

Patients receiving drug therapies that are immuno-modulatory are vulnerable to certain diseases such as progressive multifocal leukoencephalopathy (PML). For example, PML has been reported in patients treated with natalizumab. It has been found that one method of treating such subjects is to reduce the amount (e.g., plasma concentration) of the immuno-modulatory therapeutic agent (e.g., natalizumab) in the patient. Because of the rapid progression of the disease and the wide geographic distribution of patients, as well as other issues, there is a need for a rapid, reliable test that can be used to determine the level of the drug in the patient. It is an advantage for the test to be formatted so it can be administered and accurately interpreted within a short period of time. This is a particular issue with an immuno-modulatory therapy, which may be difficult to distinguish from a patient's own antibodies. Accordingly, this problem has been solved by using a rapid test design that can accurately and easily be used by physicians to determine whether the level of an immuno-modulatory therapy has been sufficiently modulated to increase the likelihood of mitigating the progression of an active case of PML. By varying the dosage of the immuno-modulatory therapy, the progression of a patient's disease state can be alleviated. Because variance of the dosage of the immuno-modulatory therapy is important for treatment, assays described herein can also be used to rapidly monitor drug level in a patient, for example, in multiple sclerosis patients including pediatric patients. In another embodiment, assays provided herein can detect anti-integrin antibodies in a subject who was treated with a natalizumab and has been diagnosed with or is suspected of having a JC virus infection. The JC virus is a type of human polyomavirus which can cause PML and other diseases in patients with immunodeficiency or in patients treated with drug intended to induce a state of immunosuppression (e.g. organ transplant patients).

In addition, assays are provided herein to detect anti-drug antibodies. The presence of such antibodies in a subject may impact drug exposure and/or result in infusion related adverse events, for example, as has been reported upon treatment with a humanized anti-VLA-4 antibody. Therefore, assays for the detection of anti-drug antibodies (e.g., the drug being the anti-VLA-4 antibody; the anti-drug antibodies being anti-anti-VLA-4 antibodies) can be useful for treatment using the drug of interest (e.g., an anti-VLA-4 drug such as a natalizumab).

In general, the apparatus is a solid substrate associated with a capture agent that can be used to specifically detect the immuno-modulatory therapeutic agent (e.g., natalizumab) or antibodies against an immuno-modulatory agent (e.g., anti-drug antibody such as antibodies against natalizumab). In some cases, the detection is calibrated to provide a method of determining whether the amount of immuno-modulatory therapeutic agent or anti-drug antibody is above or below a specified concentration or titer. Such information can be correlated with whether additional therapy (e.g., plasmapheresis) is needed to further reduce the amount of the immuno-modulatory therapeutic agent in the patient, thereby mitigating the risk associated with PML.

Also provided herein is a kit suitable for testing for the presence of an immuno-modulatory therapeutic agent such as natalizumab, or antibodies against such an immuno-modulatory therapeutic reagent. A kit will generally include at least one reagent or apparatus as described herein for detecting the immuno-modulatory therapeutic agent or antibodies against an immuno-modulatory agent. The kit can also include instructions for use of the reagents and/or apparatus. Such instructions can also include use of the kit for determining an amount of an analyte and interpretation of assay results. For example, the instructions can provide guidance as to whether detection of a specified level of a natalizumab is sufficient to treat a subject having or suspected of having PML.

Apparatus for Assaying Analytes

Various analytical devices are known to those of skill in the art, and such analytical devices can be adapted to utilize one or more capture agents, e.g., an antibody described herein, to assay one or more analytes, e.g., an anti-integrin antibody such as an anti-VLA-4 (e.g., a natalizumab), e.g., an anti-drug antibody (e.g., anti-natalizumab) described herein. Nonlimiting examples include dipstick or tester, lateral flow, dual flow and flow-through devices, particularly those that are immunoassays. Non-limiting examples of lateral flow devices include those described in U.S. Pat. Nos. 4,818,677, 4,943,522, 5,096,837 (RE 35,306), 5,096,837, 5,118,428, 5,118,630, 5,221,616, 5,223,220, 5,225,328, 5,415,994, 5,434,057, 5,521,102, 5,536,646, 5,541,069, 5,686,315, 5,763,262, 5,766,961, 5,770,460, 5,773,234, 5,786,220, 5,804,452, 5,814,455, 5,939,331, 6,306,642, each of which is incorporated by reference in its entirety. Other non-limiting examples of lateral flow devices include U.S. Pat. Nos. 4,703,017, 6,187,598, 6,352,862, 6,485,982, 6,534,320 and 6,767,714, each of which is incorporated by reference in its entirety. Non-limiting examples of dipstick devices include those described in U.S. Pat. Nos. 4,235,601, 5,559,041, 5,712,172 and 6,790,611, each of which is incorporated by reference in its entirety.

An apparatus for assaying the level of an analyte can include a substrate, e.g., a substrate with which a capture agent is associated. Non-limiting examples of substrates include glass, polystyrene, polypropylene, polyethylene, dextran, nylon, amylases, natural and modified celluloses, polyacrylamides, agarose, and magnetite. The substrate can have any structural configuration so long as the capture agent is capable of binding to an analyte.

In some instances, the substrate is housed in a support, e.g., a support that is spherical, as in a bead, or cylindrical, as in the inside surface of a test tube, or the external surface of a rod. Alternatively, the substrate or support can be flat, such as a sheet, culture dish, test strip, and the like.

In one example, the apparatus is a lateral flow apparatus that includes a sample receiving zone, a label zone, a test zone and a control zone. In some instances, a test region comprises the test and control zones. In some instances, the test region, which comprises the test and control zones, is observable.

In certain examples, the sample receiving zone accepts a fluid sample that may contain one or more analytes of interest. In another example, the sample receiving zone is dipped into a fluid sample. A label zone is located downstream of the sample receiving zone, and contains one or more mobile labeled reagents that recognize, or are capable of binding, one or more analytes of interest. Further, a test region is disposed downstream from the label zone, and contains test and control zones. The test zone(s) generally contain a capture agent associated with the substrate at the test zone. In certain instances, the capture agent is immobilized on the substrate at the test zone. Generally, the immobilized capture agent specifically binds to the analyte of interest.

As the fluid sample flows along the substrate, the analyte of interest will first bind with a mobilizable labeled reagent in the label zone, and then become restrained in the test zone. In some examples, the test region is comprised of a material that is opaque in a dry state and transparent in a moist state. Thus, when a control zone comprising a mark on the device is utilized, this mark is positioned about the test region such that it becomes visible within the test region when the test region is in a moist state.

In another instance, the fluid sample flows along a flow path running from the sample receiving zone (upstream), through the label zone, and then to the test and control zones (together comprised in a test region) (downstream). Optionally, the fluid sample may thereafter continue to the absorbent zone.

In another example, the sample receiving zone is composed of an absorbent application pad. Suitable materials for manufacturing absorbent application pads include, but are not limited to, hydrophilic polyethylene materials or pads, acrylic fiber, glass fiber, filter paper or pads, desiccated paper, paper pulp, fabric, and the like. For example, the sample receiving zone may be composed of a material such as a nonwoven spunlaced acrylic fiber (e.g., available from DuPont Nonwovens) or HDK material (available from HDK Industries, Inc., Rogersville, Tenn.). In another example, the sample receiving zone is constructed from any material that is capable of absorbing water.

In other examples, the test device is configured to perform an immunological assay. In some instances, the liquid transport along the substrate is based upon capillary action. In another situation, the liquid transport along the substrate is based on non-bibulous lateral flow, wherein all of the dissolved or dispersed components of the liquid sample are carried at substantially equal rates and with relatively unimpaired flow laterally through the substrate, as opposed to preferential retention of one or more components as would occur, e.g., in materials that interact, chemically, physically, ionically or otherwise with one or more components (see, for example, U.S. Pat. No. 4,943,522, which is incorporated by reference in its entirety).

The labeling zone of immunoassay devices can also include control-type reagents. These labeled control reagents often comprise detectable moieties that will not become restrained in the test zones and that are carried through to the test region and control zone(s) by fluid sample flow through the device. In some instances, these detectable moieties are coupled to a member of a specific binding pair to form a control conjugate that can then be restrained in a separate control zone of the test region by a corresponding member of the specific binding pair to verify that the flow of liquid is as expected. The visible moieties used in the labeled control reagents can be the same or different color, or of the same or different type, as those used in the analyte of interest specific labeled reagents.

The test region generally includes a control zone that is useful to verify that the sample flow is as expected. Each of the control zones can comprise a spatially distinct region that can include an immobilized member of a specific binding pair that reacts with a labeled control reagent. In some examples, the procedural control zone contains an authentic sample of the analyte of interest, or a fragment thereof. In this instance, one type of labeled reagent can be utilized, wherein fluid sample transports the labeled reagent to the test and control zones; and the labeled reagent not bound to an analyte of interest will then bind to the authentic sample of the analyte of interest positioned in the control zone. In another example, the control line contains antibody that is specific for, or otherwise provides for, the immobilization of the labeled reagent. In operation, a labeled reagent is restrained in each of the one or more control zones, even when any or all the analytes of interest are absent from the test sample.

Capture Agents

Various capture agents can be used in the methods and apparatus described herein, provided the capture agent specifically binds an analyte of interest to form a capture agent/analyte complex. In certain instances, the capture agent is an antigen, e.g., an integrin, and the analyte of interest is an antibody, e.g., an anti-integrin antibody or an alpha 4 integrin binding antibody (e.g. natalizumab) or an anti-drug antibody, e.g., anti-anti-VLA4 integrin chain antibody.

In some situations, the capture agent is a polypeptide, e.g., an antibody, that binds to an analyte of interest. Any antibody that specifically binds to an analyte can be utilized as a capture agent. For example, the antibody can be a polyclonal antibody; a monoclonal antibody or antigen binding fragment thereof; a modified antibody such as a chimeric antibody, reshaped antibody, humanized antibody, or fragment thereof (e.g., Fab', Fab, $F(ab')_2$); or a biosynthetic antibody, e.g., a single chain antibody, single domain antibody (DAB), Fv, single chain Fv (scFv), or the like.

Methods of making and using polyclonal and monoclonal antibodies are described, e.g., in Harlow et al., *Using Antibodies: A Laboratory Manual: Portable Protocol I.* Cold Spring Harbor Laboratory (Dec. 1, 1998), which is incorporated by reference in its entirety. Methods for making modified antibodies and antibody fragments (e.g., chimeric antibodies, reshaped antibodies, humanized antibodies, or fragments thereof, e.g., Fab', Fab, $F(ab')_2$ fragments); or biosynthetic antibodies (e.g., single chain antibodies, single domain antibodies (DABs), Fv, single chain Fv (scFv), and the like), are known in the art and can be found, e.g., in Zola, *Monoclonal Antibodies: Preparation and Use of Monoclonal Antibodies and Engineered Antibody Derivatives*, Springer Verlag (Dec. 15, 2000; 1st edition), which is incorporated by reference in its entirety.

In particular instances, the capture agent is an antibody that can specifically bind an anti-integrin antibody (e.g., an anti anti-VLA-4 antibody such as an anti-natalizumab), such as the rat 12C2 antibody, murine 12C4 antibody, or a suitable rabbit antibody. In another embodiment, the capture agent is an anti-VLA-4 antibody, such as natalizumab, that can specifically bind to an anti-(anti-VLA-4 antibody) antibody.

Analytes

The methods and apparatus described herein can be used to assay the level of an analyte of interest, e.g., in a biological sample from a subject. Exemplary analytes include, without limitation, toxins, organic compounds, polypeptides, microorganisms, bacteria, viruses, amino acids, nucleic acids, carbohydrates, hormones, steroids, vitamins, drugs (including those administered for therapeutic purposes as well as those administered for illicit purposes), pollutants, pesticides, and metabolites of or antibodies to any of the above substances. Any antigenic substance, hapten, antibody, macromolecule, and combinations thereof, can also be an analyte assayed using a method or an apparatus described herein. In particular instances, the analyte is an antibody, such as an anti-integrin antibody.

Integrins are known in the art (see, e.g., Takeda et al., Genome Biol. 8:215 (2007)), which is incorporated by reference in its entirety, and the level of any anti-integrin antibody can be assayed using a method or an apparatus described herein. An antibody can be, e.g., a polyclonal antibody; a monoclonal antibody or antigen binding fragment thereof; a modified antibody such as a chimeric antibody, reshaped antibody, humanized antibody, or fragment thereof (e.g., Fab', Fab, $F(ab')_2$); or a biosynthetic antibody, e.g., a single chain antibody, single domain antibody (DAB), Fv, single chain Fv (scFv), or the like. The antibody can be naturally produced by the subject or one that is administered to the subject.

In some instances, the analyte is an anti-VLA-4 antibody, e.g., a humanized anti-VLA-4 antibody, for example a natalizumab. TYSABRI® and other biologically active analogues, variants or derivatives of TYSABRI®, including biosimilars and biologics substantially similar thereto, qualify as a natalizumab. In particular situations, the analyte is an anti-VLA-4 antibody previously administered to the subject, e.g., as a therapeutic antibody. The analyte can be, for example, a natalizumab. In another situation, the analyte is an anti-(anti-VLA-4 antibody) antibody. The analyte can be, for example, anti-natalizumab antibody.

Biological Samples

Biological samples to be assayed for the presence of analyte using the methods and apparatus described herein can be obtained from any subject, e.g., a human or a non-human subject. In some embodiments, the biological sample is obtained from a living human subject.

In some instances, the subject from whom the sample is obtained is apparently healthy, where the assay is performed as a part of routine screening. In other embodiments, the subject has been provisionally diagnosed as having a disease or disorder and has undergone treatment, e.g., with an anti-integrin antibody, e.g., an anti-VLA-4 antibody. The biological sample can be from a subject who has been treated to decrease the amount of analyte. In some cases, a sample from a subject is tested using a method described herein before the subject undergoes a treatment, e.g., to modulate the amount of analyte in the subject or to establish the baseline level of analyte in the subject or to establish the suitability of the treatment, and after the subject has been treated, e.g., to monitor and/or to modulate the amount of analyte in the subject.

The biological sample can be derived from any tissue, organ or group of cells of the subject. In some circumstances, the biological sample is a cervical scrape, biopsy, or lavage obtained from a subject. In other instances, the sample is a blood, plasma, serum, or urine sample.

In some situations, the biological sample can be processed, e.g., to remove certain components that may interfere with a method described herein, using methods that are known in the art. For example, the biological sample can be processed to be enriched for proteins, e.g., by salt precipitation, and the like.

In certain methods described herein, the level of an analyte in a sample can be quantified and/or compared to controls. Suitable control samples can be, e.g., from individuals who have not received a treatment, e.g., an anti-integrin antibody treatment, e.g., an anti-VLA-4 antibody treatment. Control samples can be from individuals genetically related to the subject being assayed, but can also be from genetically unrelated individuals. In some cases, the control is an established reference. In other instances, the level of an analyte, e.g., an anti-integrin antibody, is quantified using known methods. In yet other situations, the presence or absence of an analyte, e.g., an anti-integrin antibody, within a sample is determined by visual inspection of the assay.

In certain embodiments, a sample is contacted to a solid support-bound capture agent under conditions suitable for binding of the capture agent to analytes in the sample, and, after separation of unbound sample analytes from the bound analytes, the bound analytes are detected as described herein.

Methods of Assaying

In some situations, an analyte, e.g., an anti-integrin antibody, e.g., an anti-VLA-4 antibody, or e.g., an anti-(anti-VLA-4 antibody) antibody, can be assayed using a method selected from a variety of immunoassay methods, both qualitatively and quantitatively Immunological and immunoassay procedures are known and described in, e.g., Stites et al. (eds.) *Basic and Clinical Immunology* (4th ed.) Lange Medical Publications, Los Altos, Calif., which is incorporated by reference in its entirety. Immunoassays can be performed in any of several configurations known in the art and described in, e.g., Maggio Enzyme Immunoassay, CRC Press, Boca Raton, Fla. (1980); Tijssen, "Practice and Theory of Enzyme Immunoassays," *Laboratory Techniques in Biochemistry and Molecular Biology*, Burdon and van Knippenberg Eds., Elsevier (1985), pp 9-20; and Harlow and Lane, *Antibodies, A Laboratory Manual*, Cold Spring Harbor Publications, NY (1988), each of which is incorporated by reference in its entirety.

Immunological Binding Assays

In some instances, an analyte, e.g., an anti-integrin antibody, or e.g., an anti-drug antibody, is detected and/or quantified using any of a number of known immunological binding assays (see, e.g., U.S. Pat. Nos. 4,366,241; 4,376,110; 4,517,288; 4,837,168; and Asai, Methods in Cell Biology Volume 37: Antibodies in Cell Biology, Academic Press, Inc. NY (1993), each of which is incorporated by reference in its entirety).

Immunoassays can also utilize a labeled reagent to specifically bind to and label the capture agent/analyte complex. The labeled reagent may itself be one of the moieties comprising the capture agent/analyte complex. Alternatively, the labeled reagent may be a third moiety, such as an antibody, that specifically binds to the analyte or the capture agent/analyte complex.

In some situations, the analyte is an antibody, e.g., an anti-integrin antibody, or e.g., an anti-drug antibody, and the labeled reagent is a second antibody bearing a label. Alternatively, the second antibody may lack a label, but it may, in turn, be bound by a labeled reagent that includes a third antibody specific to antibodies of the species from which the second antibody is derived. The second antibody can be modified with a detectable moiety, such as biotin, to which a labeled reagent can specifically bind, such as enzyme-labeled streptavidin.

Other proteins that can specifically bind immunoglobulin constant regions, such as protein A or protein G, can also be used as the labeled reagent. These proteins are normal constituents of the cell walls of streptococcal bacteria. They exhibit a strong non-immunogenic reactivity with immunoglobulin constant regions from a variety of species (see, e.g., Kronval et al., J. Immunol. 111:1401-1406 (1973); and Akerstrom et al., J. Immunol. 135:2589-2542 (1985), which is incorporated by reference in its entirety).

Throughout the methods and assays described herein, incubation and/or washing steps may be required after one or more combination of reagents. Incubations carried out during the assay can vary from about 5 seconds to several hours, in general, from about 5 minutes to about 24 hours. The incubation time will depend upon the assay format, analyte, volume of solution, concentrations, and the like. In general, an assay is carried out at ambient temperature, although an assay can be conducted over a range of temperatures, such as about 4° C. to about 40° C., e.g., 4° C.-10° C., or 4° C.-25° C.

1. Non-Competitive Assay Formats

Immunoassays for detecting an analyte of interest, e.g., an anti-integrin antibody, or e.g., an anti-drug antibody, from samples can be competitive or noncompetitive. Noncompetitive immunoassays are assays in which the amount of analyte in a capture agent/analyte complex is directly measured. In a "sandwich" assay, for example, the capture agent can be bound directly to a solid substrate where it is immobilized. These immobilized capture agents can then specifically bind an analyte present in a test sample. The analyte, e.g., anti-integrin antibody, or e.g., an anti-drug antibody, thus immobilized is then bound by a labeled reagent, such as a second antibody bearing a label. Alternatively, the second antibody may lack a label, but it may, in turn, be bound by a labeled reagent that is a third antibody specific to antibodies of the species from which the second antibody is derived. The second antibody can be modified with a detectable moiety, such as biotin, to which a third labeled reagent can specifically bind, such as enzyme-labeled streptavidin.

2. Competitive Assay Formats

In competitive assays, the amount of analyte (such as an anti-integrin antibody or an anti-drug antibody) present in a sample is measured indirectly by measuring the amount of an added (exogenous) analyte displaced (or competed away) from a capture agent (e.g., an antibody specific for the analyte) by the analyte present in the sample. In one competitive assay, a known amount of an analyte, e.g., anti-integrin antibody, or e.g., an anti-drug antibody, is added to the sample and the sample is then contacted with a capture agent, e.g., an antibody that specifically binds to an anti-integrin antibody: The amount of analyte bound to the capture agent, e.g., antibody, is inversely proportional to the concentration of analyte present in the sample. In a particular example, the capture agent, e.g., an antibody that binds to an anti-integrin antibody, is immobilized on a solid substrate. For example, the amount of the analyte, e.g., anti-integrin antibody, or e.g., an anti-drug antibody, bound to the capture agent, e.g., antibody that binds an anti-integrin antibody, or e.g., drug that anti-drug antibody binds to, may be determined either by measuring the amount of analyte present in a capture agent/analyte complex or, alternatively, by measuring the amount of remaining uncomplexed analyte. The amount of analyte may be detected by providing a labeled reagent.

3. Other Assay Formats

In other instances, when the analyte is a polypeptide, western blot (immunoblot) analysis can be used to detect and quantify the presence of the polypeptide in a sample. The technique generally comprises separating sample proteins by gel electrophoresis on the basis of molecular weight, transferring the separated proteins to a suitable solid support (such as, e.g., a nitrocellulose filter, a nylon filter, or a derivatized nylon filter), and incubating the sample with the antibodies that specifically bind the polypeptide of interest. For example, the antibodies specifically bind to a polypeptide of interest on the solid support. These antibodies may be directly labeled or alternatively may be subsequently detected using labeled antibodies (e.g., labeled sheep anti-mouse antibodies) that specifically bind to the antibodies against the polypeptide of interest.

Other assay formats include liposome immunoassays (LIA), which use liposomes designed to bind specific molecules (e.g., antibodies) and release encapsulated reagents or markers. The released chemicals are then detected according to standard techniques (see, e.g., Monroe et al., Amer. Clin. Prod. Rev. 5:34-41(1986), which is incorporated by reference in its entirety).

4. Labeled Reagents

The detectable label used in a method or apparatus described herein is not limiting as long as it does not significantly interfere with the specific binding of the labeled reagent used in the method or apparatus. The detectable label can be any material having a detectable physical or chemical property. Such detectable labels have been well developed in the field of immunoassays and, in general, most labels useful in such methods can be used in the methods and apparatus described herein. A label can be, e.g., any composition detectable by spectroscopic, photochemical, biochemical, immunochemical, electrical, optical or chemical means. Useful labels in the methods and apparatus described herein include, without limitation, magnetic beads (e.g., Dynabeads™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horseradish peroxidase, alkaline phosphatase and others that can be used in an ELISA), and colorimetric or particulate labels such as colloidal gold or colored glass or plastic (e.g., polystyrene, polypropylene, latex, etc.) beads.

The label can be coupled directly or indirectly to the desired component of the assay according to methods known in the art. As described herein, a wide variety of labels can be used, with the choice of label depending on the sensitivity required, the ease of conjugation, stability requirements, available instrumentation, and disposal provisions.

Non-radioactive labels can be attached by indirect means. Molecules can also be conjugated directly to signal generating compounds, e.g., by conjugation with an enzyme or fluorescent compound. A variety of enzymes and fluorescent compounds can be used with the methods and apparatus described herein and are well-known to those of skill in the art (see, e.g., U.S. Pat. No. 4,391,904, which is incorporated by reference in its entirety).

Means of detecting labels are known to those of skill in the art. Thus, for example, where the label is a radioactive label, means for detection include a scintillation counter or photographic film as in autoradiography. Where the label is a fluorescent label, it can be detected by exciting the fluorochrome with the appropriate wavelength of light and detecting the resulting fluorescence. The fluorescence can be detected visually, by means of photographic film, by the use of electronic detectors such as charge-coupled devices (CCDs) or photomultipliers and the like. Similarly, enzymatic labels can be detected by providing the appropriate substrates for the enzyme and detecting the resulting reaction product. Finally simple colorimetric labels can be detected directly by observing the color associated with the label. Thus, in various dipstick assays, conjugated gold often appears pink, while various conjugated beads appear the color of the bead.

Some assay formats do not require the use of labeled reagents. For instance, agglutination assays can be used to detect the presence of target antibodies. In this case, antigen-coated particles are agglutinated by samples comprising target antibodies. In this format, none of the assay components need to be labeled, and the presence of the target antibody is detected by simple visual inspection.

After detection of a detectable signal, the signal can be compared to a reference and/or correlated with a predetermined level corresponding to treatment recommendations. For example, in an assay to detect the level of an anti-VLA-4 antibody in a subject being treated with plasmapheresis to reduce the amount of the antibody, a level of signal below a predetermined level may be correlated with a recommendation that further plasmapheresis is not required. A signal correlated with a higher level may indicate that additional plasmapheresis is advisable.

Detection of signal in an assay described herein can be visual, but may also be performed using a reader to detect a signal. Such readers include, for example, automated plate readers, EIA readers, and the like. Readers can be used for semi-quantitative or quantitative determination of the concentration for tested analytes. Semi-quantitative or quantitative determination of concentration can be depicted using a colorimetric system.

5. Secondary Agents

The secondary agents used in a method or apparatus described herein can be used to detect binding of the capture agent to the antibody, The secondary agent can be an antibody that has a detectable label attached, either covalently or non-covalently. The detectable label attached to the secondary agent can be a detectable label as previously described. The secondary agent can be a non-specific antibody, or antibodies that recognize the analyte or fragments thereof or polypeptides that recognize the analyte. The secondary agent can include anti-IgG4 antibody, for example, anti-human IgG4 or anti-human IgG4 that reacts with the Fc portion of the heavy chain of human IgG4.

6. Time

Binding of the capture agent to the antibody can be detectable within about 30 seconds, 1 minute, 5 minutes, 10 minutes, 20 minutes, 30 minutes, 40 minutes, 50 minutes, 1 hour, 2 hours, 5 hours, or 10 hours after the binding.

7. Buffer

Any suitable buffer for immunological assays can be used as a chase buffer as determined by a person of skill in the art. The chase buffer can include a surfactant. Any suitable surfactant can be used. A surfactant can be a polysorbate surfactant such as TWEEN 20®, TWEEN 40®, TWEEN 60®, TWEEN 80®, SPAN 20®, SPAN 40®, SPAN 60®, SPAN 65®, and SPAN 80®. The buffer can also include a buffered saline, such as Tris buffered saline (TBS) or phosphate buffered saline (PBS). The buffer can also include a blocking agent, for example a protein such as bovine serum albumin (BSA), milk or gelatin.

Treatments

The assays described herein can be performed before and/or after administering a treatment to a subject. In some instances, the treatment is a treatment to remove an analyte or component from the subject, such as from the blood of a subject. In particular situations, the treatment is blood apheresis, such as plasma exchange, to remove one or more antibodies from the subject.

Blood apheresis is a common medical use of continuous fluid separation. Apheresis has many clinical uses, including multiple therapies that involve removing blood from a subject's body, separating the blood into components, altering one or more of the components, and putting some mixture or selection from the removed and/or altered fluid back into the subject's body. Some exemplary therapeutic apheresis procedures include therapeutic plasma exchange (TPE or PLEX) (a procedure by which cell-free plasma is removed and replaced with colloid/saline solution); cytoreduction (a process by which platelets and white blood cells are removed); photopheresis (a procedure by which mononuclear cells collected by therapeutic apheresis are exposed to ultraviolet-A light and psoralen, and reinfused into the subject); and selective adsorption (a process by which plasma is adsorbed on a column and returned to the subject).

In one exemplary apheresis procedure, blood is withdrawn from a subject through a needle inserted into the vein of the subject. The needle is attached to one end of a plastic tube that provides a flow path for the blood. The other end of the tube leads to a separator, such as a centrifuge, for separating the blood into its components. Flow-through centrifuges that allow for the continuous inflow and outflow of materials to and from the centrifuge are well known in the art (see, for example, U.S. Pat. No. 4,425,112, which is incorporated by reference in its entirety). The blood that is separated into plasma and cells can be returned to the subject through the other arm. A plasma substitute or an altered plasma can be recombined with the blood elements to be returned to the subject. Since the rate of blood being withdrawn from the subject and the blood returning to the subject can be at the same rate, only a small amount of the subject's blood can be outside of the body at any time.

Another apheresis procedure utilizes an automated system that uses disposable, pre-sterilized fluid circuits through which the blood flows. The fluid circuits are mounted on reusable machines that may have pumps, valves, sensors, and the like. These automated systems further include an internal computer and associated software programs that control many of the processing functions. One exemplary automated system is described in U.S. Pat. No. 6,706,008, which is incorporated by reference in its entirety. Other methods and apparatus for apheresis are described in, e.g., U.S. Pat. Nos. 7,267,771; 6,849,183; 5,200,090; and 4,954,128, each of which is incorporated by reference in its entirety.

In some situations, the level of an anti-integrin antibody or an anti-drug antibody described herein is assayed before administering a treatment to a subject. In other situations, the level of an anti-integrin antibody or an anti-drug antibody is assayed after administering a treatment to a subject. For example, the level of an anti-integrin antibody or anti-drug antibody is assayed one day, two days, three days, four days, five days, six days, one week, two weeks, three weeks, or four weeks after the administration of the treatment. Such assays can be administered as part of a treatment regime, for example to periodically monitor drug levels or levels of anti-drug antibodies. In certain instances, the treatment is administered and the level of an anti-integrin antibody or anti-drug antibody assayed in repeated cycles of treatment and assay, for example, until the level of the anti-integrin antibody in the sample reaches a predetermined level. For example, the predetermined level can be about 1 µg/ml, about 2 µg/ml, about 3 µg/ml, about 4 µg/ml, about 5 µg/ml, about 6 µg/ml, about 7 µg/ml, about 8 µg/ml, about 9 µg/ml, about 10 µg/ml, about 15 µg/ml, or about 20 µg/ml. In some cases, the predetermined level is 1 µg/ml, 2 µg/ml, 3 µg/ml, 4 µg/ml, 5 µg/ml, 6 µg/ml, 7 µg/ml, 8 µg/ml, 9 µg/ml, 10 µg/ml, 15 µg/ml, or 20 µg/ml. The treatments can be administered, e.g., once a day, or once every two days, three days, four days, five days, six days, one week, two weeks, three weeks, four weeks, every three months, every four months, every six months, or annually.

The invention is further illustrated by the following examples. The examples are provided for illustrative purposes only. They are not to be construed as limiting the scope or content of the invention in any way.

EXAMPLES

Example 1

Development of a Test to Assay Anti-VLA-4 Antibody in Buffer Using Rat 12C2 mAb or Mouse 12C4 mAb and Anti-human IgG4-Gold Conjugates

A lateral flow immunochromatographic test system was used to develop an anti-VLA-4 specific test. Referring to FIG. 1, the lateral flow test system was composed of a two part plastic cassette (top 100 and bottom 101). The top part contained two openings—one opening 102 for the application of samples 110 and chase buffer 118 and a window 103 for visual detection of the results. The lower part accommodated a nitrocellulose test strip 104 on which the rat 12C2 mAb or mouse 12C4 mAb 105 was immobilized at a "test site" ("T") 106 and a universal gold capture reagent 107 at a "control site" ("C") 108.

Upstream from the test and control sites, there was a "gold pad" 109 of fibrous material where a mouse anti-human IgG4 was conjugated to gold particles, the complex being 112. Further upstream from the gold conjugate pad was another fibrous pad 111 that received the sample humanized anti-VLA-4 antibody in buffer (110) and chase buffer 118 via opening 102. The sample pad 111, gold pad 109, and nitrocellulose membrane 104 were in sequential order so that the sample migrated by capillary action from the sample pad 111 to the gold pad 109 to form a "first complex" of sample 110 and mouse anti-human IgG4/gold conjugate 112. The complex then traveled through the nitrocellulose 104 where it encountered the mouse 12C4 mAb or rat 12C2 mAb 105 at the test site 106. The sample 110 reacted with the mouse 12C4 mAb or rat 12C2 mAb 105, forming a complex of 112 and 110 that was arrested at the test site 106 and was visualized as a red line 114. In another embodiment, the sample 110 can be added downstream of the gold conjugate.

Excess gold labeled free antibody (mouse anti-human IgG4) traveled further to the control site where a universal gold capture reagent 107 captured the gold-labeled free antibody (mouse anti-human IgG4), giving rise to an additional visible red line 115 at control site 108. Any excess material, gold, and chase buffer was absorbed at the distal end of the nitrocellulose strip by an absorbent filter pad 116.

The specificity of the test was due to the fact that the complex at the test site only formed when the sample molecule contains a human or humanized IgG4 moiety to capture the mouse anti-human IgG4 gold conjugate and form the first complex and the anti-VLA-4 moiety to react with the anti-(anti-VLA-4 antibody) antibody at the test site. In a simplistic representation, the anti-VLA-4 molecule is sandwiched between the gold labeled mouse anti-human IgG4 and the membrane immobilized anti-(anti-VLA-4 antibody) antibody.

Materials

Mouse anti-(anti-VLA-4 antibody) mAb 12C4 (Elan), 2.1 mg/mL

Rat anti-(anti-VLA-4 antibody) mAb 12C2 (Biogen Idec), 1.76 mg/mL

Mouse anti-human IgG4 mAb (Southern Biotech), 0.5 mg/mL

Humanized anti-VLA-4 Ab (Biogen Idec), 20 mg/mL

Anti-VLA-1 Ab (Biogen Idec),

Human IgG4 (CalBiochem), 1 mg/mL

Humanized anti-VLA-4 Ab formulation buffer (Biogen Idec)

Universal gold capture reagent

Chase buffer (PBS with 1% w/v BSA and 1% w/v Tween 20)

Gold conjugate (40 nm)

Test Development

The approach for developing the anti-VLA-4 antibody test was to target the antigen binding site with a capture antibody specific for the anti-VLA-4 antibody (mAb 12C4 or 12C2) immobilized on the membrane, and a gold labeled detector antibody (anti-human IgG4) directed against the constant region of the anti-VLA-4 antibody, which comprises a human IgG4 molecule.

If the monoclonal antibody 12C4 or 12C2 is highly specific, no other molecule is captured on the membrane and thus the test is negative. Anti-VLA-1 is a humanized monoclonal antibody to VLA-1. The constant region of the antibody is human IgG1, while the variable antigen binding region is of mouse origin. Because VLA-1 and VLA-4 are closely related, anti-VLA-1 can be used as an additional control of the test system. Such an inclusion can be used to confirm the specificity of the test system.

Based on these assumptions, a lateral flow immunochromatographic system was developed with the mAb 12C4 or 12C2 directed against the humanized anti-VLA-4 antibody. To determine the appropriate concentration of the capture antibody, 12C4 or 12C2 was utilized, which was titrated between 0.25 and 1.0 mg/mL on separate test strips and tested against the humanized anti-VLA-4 antibody at 80 µg/mL. The 12C4 or 12C2 antibody was then immobilized at the test site of the membrane at 1.0 mg/mL. A mouse monoclonal antibody anti-human IgG4 (gamma chain specific) at 30 µg/mL was conjugated to gold particles. The mouse anti-human IgG4 immunogold conjugate was then lyophilized in the conjugate pad and utilized as a detector molecule. At the control site of the membrane, universal gold reagent at 3.0 mg/mL was utilized.

Results

During the titration of the monoclonal antibody 12C4 or 12C2, a positive reaction was indicated by the presence of a band on the top portion of each strip. The 1.0 mg/mL antibody concentration was selected, as it resulted in an intense signal with minimum background, and was immobilized at the test site of the membrane.

The humanized anti-VLA-4 antibody, humanized anti-VLA-1, IgG1 (myeloma), IgG4 (myeloma), anti-IgG1 and the formulation buffer are tested on a flow system with 12C4 or 12C2 immobilized. The humanized anti-VLA-4 antibody was tested at the concentration range of 0.015 and 500 µg/mL. The 12C4 or 12C2 antibody was able to detect the humanized anti-VLA-4 antibody to a concentration of 0.08 µg/mL.

The 12C2 antibody was then used to manufacture test cassettes. FIG. 1 illustrates the specificity of the test utilizing the test cassettes. All tests showed a single band 115, indicating a valid test, but only the cassette for the humanized anti-VLA-4 antibody test showed a second band 114 indicating a positive test.

Example 2

Development of a Test to Assay Anti-VLA-4 Antibody in Serum Using Rat 12C2 mAb or Mouse 12C4 mAb and Anti-Human IgG4-Gold Conjugates

Figure 2:
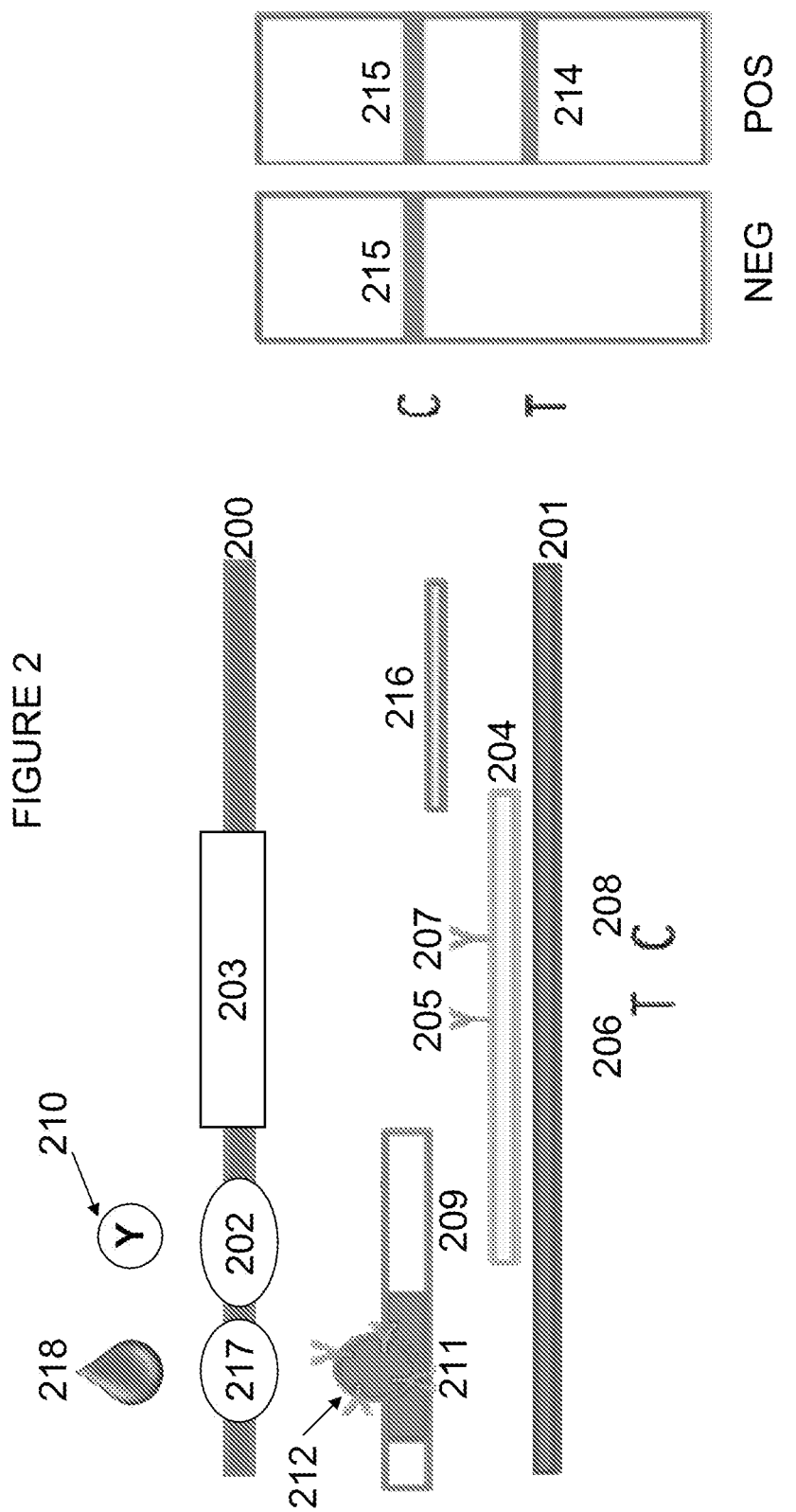
FIG. 2 is a schematic of the lateral flow apparatus and the results of a test corresponding to Example 2 following the loading of various components.

To test the viability of the test using a biological fluid, an assay was tested using serum spiked with anti-VLA-4. The two-part plastic cassette of this lateral flow test system is the same as that for Example 1 with a few alterations. Referring to FIG. 2, the top part 200 contained three openings—opening 202 is for the application of samples 210, opening 217—for chase buffer 218 and a window 203 for visual detection of the results. In other embodiments (not shown), the chase buffer can be added downstream of the sample or added at the same opening as the one for application of samples. The lower part 201 accommodated a nitrocellulose test strip 204 on which the mouse 12C4 mAb or rat 12C2 mAb 205 was immobilized at a "test site" (T) 206 and a goat anti-mouse antibody 207 at a "control site" (C) 208. In other embodiments, antibody against serum-specific analytes (e.g., serum albumin), may be utilized as control antibody.

Upstream from the test and control sites, there was a fibrous pad ("sample pad") 209 that received the sample 210. Further upstream from the test and control sites there was a "gold pad" 211 of fibrous material where a mouse anti-human IgG4 was conjugated to gold particles, the complex being 212. The two-step assay was utilized. In the first step, serum sample 210 was applied to the sample opening 202 and migrated toward the capture zone 205 ahead of the gold conjugate to form a complex of a sample 210 (anti-VLA4) with the mouse 12C4 or rat 12C2 on test line 205. In the second step, the chase buffer 218 was applied to the chase buffer port 217 rehydrated the monoclonal anti-human IgG4 gold conjugate 212. The conjugate 212 then traveled toward the capture test line 205 to form a complex with anti-VLA-4 bound to capture line 205, and the reaction at site 206 was visualized as a red line 214.

Excess gold-labeled free antibody (mouse anti-human IgG4) traveled further to the control site 208 where a goat anti-mouse antibody 207 captured the gold-labeled free antibody (mouse anti-human IgG4), giving rise to an additional visible red line 215. Any excess material, gold, and chase buffer was absorbed at the distal end of the nitrocellulose strip by an absorbent filter pad 216.

The specificity of the test was due to the fact that the complex at the test site only formed when the sample contains anti-VLA-4 moiety to react with the anti-(anti-VLA-4 antibody) antibody at the test site, and to be detected by a mouse anti-human IgG4 moiety conjugated to gold. In a simplistic representation, the anti-VLA-4 molecule is sandwiched between the gold labeled mouse anti-human IgG4 and the membrane immobilized anti-(anti-VLA-4 antibody) antibody. The success of this format is reliant upon any endogenous interfering moiety (e.g., IgG4) in the sample traveling ahead of the anti-IgG4 gold conjugate reducing its interference with the detection of the anti-VLA-4 at the test line.

A reader can be used for semi-quantitative determination of the concentration of the tested analytes. To record the results of the lateral flow system, a reader based on visual positive/negative scoring was used. The visual threshold on the reader corresponds to values within the 20-40 unit range. If the signal was recorded visually positive within this range then it should be considered a very weak pink line that may not be visible to all operators.

Materials

Mouse anti-(anti-VLA-4 antibody) mAB 12C4 (Elan), 2.1 mg/mL

Mouse anti-human IgG4 mAb (Southern Biotech), 0.5 mg/mL

Humanized anti-VLA-4 Ab (Biogen Idec), 21 mg/mL

Human IgG4 (The Binding Site, San Diego, Calif.), 13.7 mg/mL

Humanized anti-VLA-4 Ab formulation buffer (Biogen Idec)

Goat anti-mouse antibody, 3.0 mg/ml

Chase buffer (PBS with 1% w/v BSA and 1% w/v Tween 20)

Gold conjugate (40 nm)

Test Development

The approach for developing the test was to target the antigen binding site with a capture antibody (mAb 12C4 or mAb 12C2) immobilized on the membrane, specific for the anti-VLA-4 antibody, and a gold labeled detector antibody (mouse anti-human IgG4) directed against the constant region of the anti-VLA-4 antibody, which comprises a human IgG4 molecule.

If a monoclonal antibody used in the assay such as 12C4 or 12C2 is highly specific, no other analyte is captured on the membrane and therefore the test is negative.

Based on these assumptions, a lateral flow immunochromatographic system was developed with the mAb 12C4 or 12C2 directed against the humanized anti-VLA-4 antibody. To determine the appropriate concentration of the capture antibody, 12C4 was utilized, which was titrated on separate test strips and tested against the humanized anti-VLA-4 antibody at a variety of concentrations ranging from 100 μg/mL to 0.25 μg/mL. The 12C4 antibody was then immobilized at the test site of the membrane at 2.1 mg/mL. A mouse monoclonal antibody anti-human IgG4 (gamma chain specific) was conjugated to 40 nm gold particles. The mouse anti-human IgG4 immunogold conjugate was then lyophilized in the conjugate pad and utilized as a detector molecule. At the control site of the membrane, a goat anti-mouse antibody at 3.0 mg/mL was utilized.

Results

During the titration of the monoclonal antibody 12C4 or 12C2, a positive reaction was indicated by the presence of a band on the top portion of each strip. The 2.1 mg/mL antibody concentration was selected, as it resulted in an intense signal with minimum background, and was immobilized at the test site of the membrane. The protocol consisted of adding 20 μL serum (pre-diluted 1:10 in chase buffer or neat) at port 202 immediately (<1 minute) followed by 150 μL chase buffer 218 at port 217. The sample was left to incubate in device for 30 minutes at room temperature and ambient humidity.

The humanized anti-VLA-4 antibody, in sample matrix, IgG4 (myeloma), anti-VLA-4 together with IgG4, and the formulation buffer are tested on a flow system with 12C4 immobilized. The humanized anti-VLA-4 antibody was tested at the concentration range of 0.25 and 100 μg/mL. The 12C4 antibody was able to detect the humanized anti-VLA-4 antibody to a concentration of 0.25 μg/mL.

The 12C4 antibody was then used to manufacture test cassettes. FIG. 2 illustrates the specificity of the test utilizing the test cassettes. All tests showed a single band 215, indicating a valid test, but only the cassettes for the humanized anti-VLA-4 antibody test showed a second band 214 indicating a positive test.

In some embodiments, the test includes additional components. Anti-VLA-1 is a humanized monoclonal antibody to VLA-1. The constant region of some anti-VLA-1 antibodies is IgG1, while the variable antigen binding region is of mouse origin. In some embodiments, anti-VLA-1 is used as an additional control to assess specificity of the test system. Additional controls that can be included in the test system include assessing tolerance of the test to excess levels of analytes that may be found in the serum, e.g., IgG4, drug, or anti-drug antibodies. A reader can be used for semi-quantitative or quantitative measurement of anti-VLA4 concentrations.

Example 3

Figure 3:
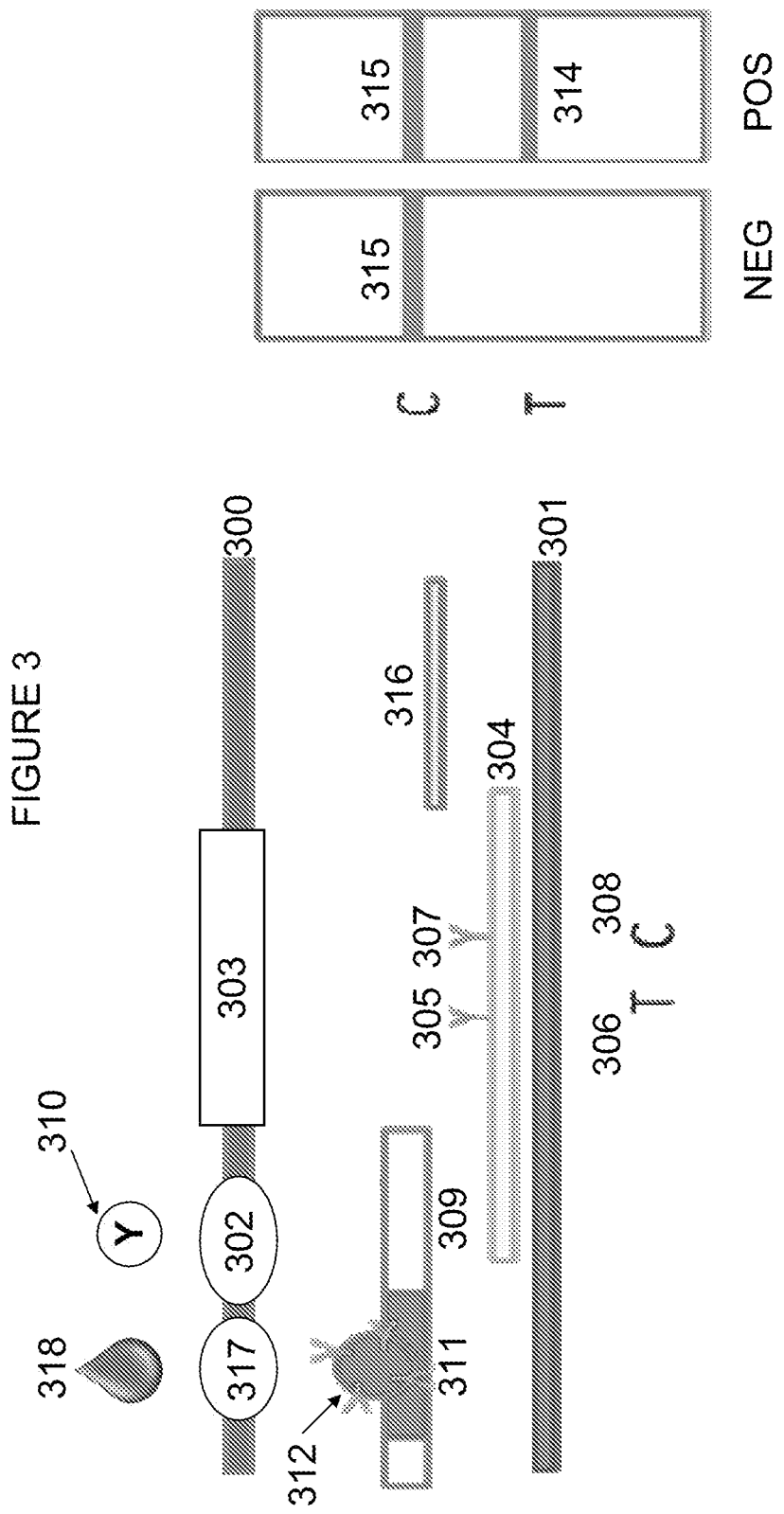
FIG. 3 is a schematic of the lateral flow apparatus and the results of a test corresponding to Example 3 following the loading of various components.

Development of a Test to Assay Anti-VLA-4 Antibody Using Anti-Anti-VLA-4 mAB-Gold Conjugates Experiments were conducted to test the ability of a different format to effectively detect anti-VLA-4 antibody in serum. The two part plastic cassette of this lateral flow test system is the same as that for Example 2 with a few alterations. Referring to FIG. 3, the top part 300 contained three openings—one 302 is for the application of samples 310, opening 317—for application of chase buffer 318 and a window 303 for visual detection of the results. The lower part 301 accommodated a nitrocellulose test strip 304 on which the mouse 12C4 mAb 305 was immobilized at a "test site" (T) 306 and a goat anti-mouse antibody 307 at a "control site" (C) 308.

Upstream from the test and control sites, there was a fibrous pad ("sample pad") 309 that received the sample 310. Further upstream from the test and control sites there was a "gold pad" 311 of fibrous material where a mouse anti-anti-VLA4 antibody 12C4 was conjugated to gold particles, the complex being 312. The two-step assay was utilized. In the first step, sample 310 was applied to the sample opening 302 and migrated toward the capture zone 305 ahead of the gold conjugate to form a complex of a sample 310 (anti-VLA4) with the mouse 12C4 or rat 12C2 on test line 305. In the second step, the chase buffer 318 was applied to the chase buffer port 317 and rehydrated the monoclonal mouse anti-anti-VLA4 antibody 12C4 gold conjugate 312. The conjugate 312 then traveled toward the capture test line 305 to form a complex with anti-VLA-4 bound to capture line 305, and the reaction at site 306 was visualized as a red line 314.

Excess gold-labeled free antibody (mouse 12C4 mAb) traveled further to the control site where a goat anti-mouse antibody 307 captured the mAb, giving rise to an additional visible red line 315. Any excess material, gold, and chase buffer was absorbed at the distal end of the nitrocellulose strip by an absorbent filter pad 316.

When using spiked natalizumab samples, this test format is more restricted in its range of detection than the test conducted with the anti-human IgG4 gold conjugate because the complex at the test site only formed when the sample molecule can react with both the anti-(anti-VLA-4 antibody)/gold conjugate and the anti-(anti-VLA-4 antibody) antibody at the test site. In a simplistic representation, the anti-VLA-4 molecule is bridging between the gold labeled anti-(anti-VLA-4 antibody) antibody and the membrane immobilized anti-(anti-VLA-4 antibody) antibody. Therefore, this test is less sensitive for overall detection of the anti-VLA-4 antibody when using actual samples from patients. This format results in a more restricted test in that it detects only intact natalizumab, which is an IgG4-based antibody. This format does not detect half-antibody exchanged molecules, which is observed in patients treated with natalizumab and other IgG4 antibodies. Therefore, the uses of this format are generally restricted to detection of intact drug.

Materials

Mouse anti-(anti-VLA-4 antibody) mAB 12C4 (Elan), 2.1 mg/mL

Humanized anti-VLA-4 Ab (Biogen Idec), 21 mg/mL

Humanized anti-VLA-4 Ab formulation buffer (Biogen Idec)

Goat anti-mouse antibody, 3.0 mg/ml

Chase buffer (PBS with 1% w/v BSA and 1% w/v Tween 20)

Gold conjugate (40 nm)

Test Development

A lateral flow immunochromatographic system was developed with the mAb 12C4 directed against the humanized anti-VLA-4 antibody. To determine the appropriate concentration of the capture antibody, 12C4 was titrated on separate test strips and tested against the humanized anti-VLA-4 antibody at the concentrations ranging from 0.25 to 100 µg/mL. The 12C4 antibody was then immobilized at the test site of the membrane at 2.1 mg/mL. Also, 12C4 antibody was conjugated to 40 nm gold particles, lyophilized in the conjugate pad and utilized as a detector molecule. At the control site of the membrane, a goat anti-mouse antibody at 3.0 mg/mL was utilized.

Results

During the titration of the monoclonal antibody 12C4, a positive reaction was indicated by the presence of a band on the top portion of each strip. The 2.1 mg/mL antibody concentration was selected, as it resulted in an intense signal with minimum background, and was immobilized at the test site of the membrane. The protocol consisted of adding 20 µL serum (pre-diluted 1:10 in chase buffer or neat) at port 302 immediately (<1 minute) followed by 150 µL chase buffer 318 at port 317. The sample was left to incubate in device for 30 minutes at room temperature and ambient humidity.

The humanized anti-VLA-4 antibody in matrix, anti-VLA-4 antibody with additional IgG4 added and the formulation buffer were tested on a flow system with 12C4 immobilized. The humanized anti-VLA-4 antibody was tested at the concentration range of 1 and 100 µg/mL. The 12C4 antibody was able to detect the humanized anti-VLA-4 antibody to a concentration of 1 µg/mL.

The 12C4 antibody was then used to manufacture test cassettes. FIG. 3 illustrates the specificity of the test utilizing the test cassettes. All tests showed a single band 315, indicating a valid test, but only the cassette for the humanized anti-VLA-4 antibody test showed a second band 314, indicating a positive test.

Example 4

Figure 4:
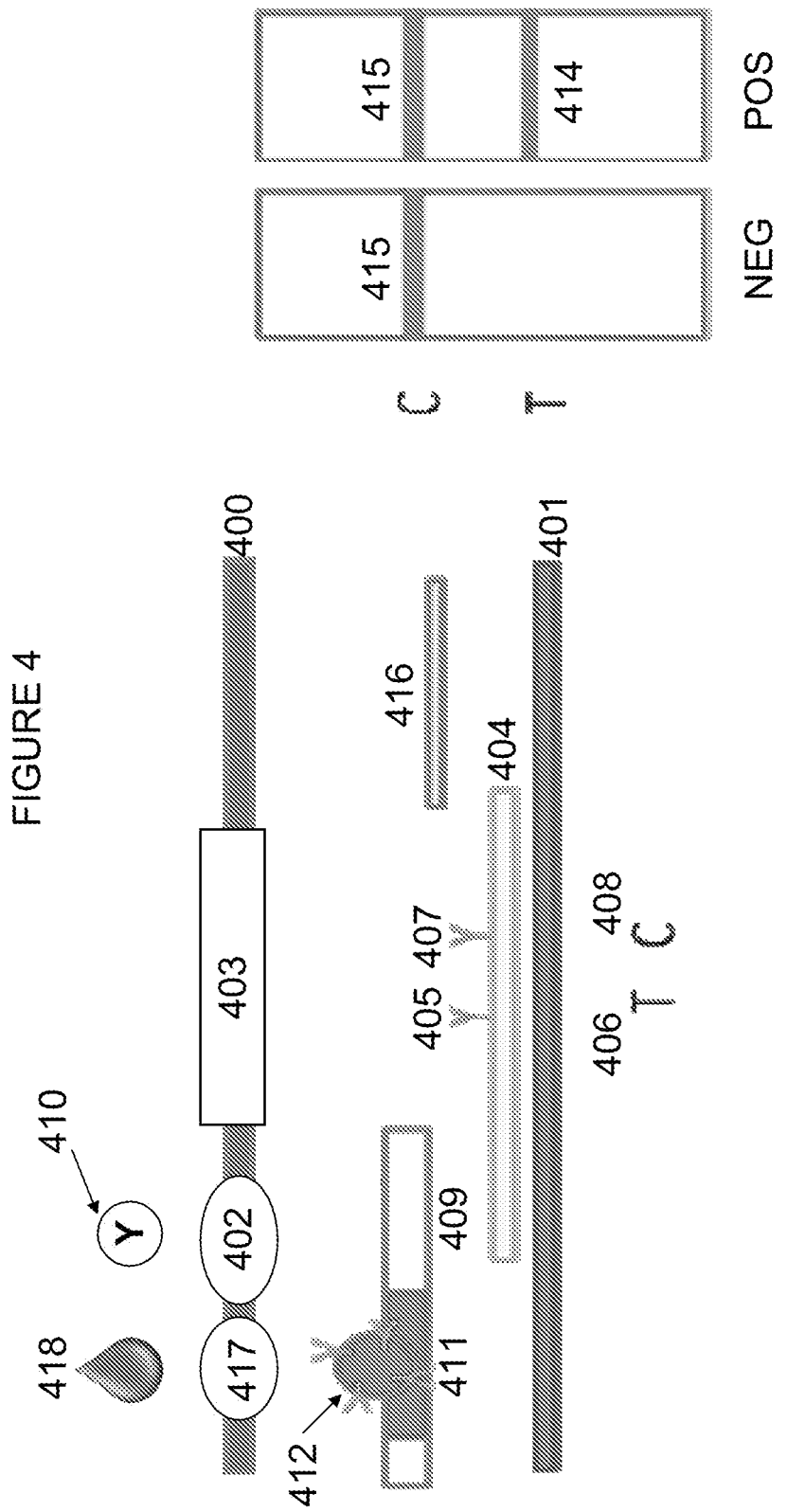
FIG. 4 is a schematic of the lateral flow apparatus and the results of a test corresponding to Example 4 following the loading of various components.

Development of a Test to Assay Anti-Drug Antibody Using Anti-VLA-4 Drug and Anti-VLA-4 Drug Gold Conjugate Assays and methods to detect antibodies directed against a drug, e.g., natalizumab are described herein. To test such an assay, the two-part plastic cassette of this lateral flow test system was the same as that for Examples 1-3 with a few alterations. Referring to FIG. 4, the top part 400 contained three openings—opening 402 for the application of samples 410, opening 417—for chase buffer 418 and a window 403 for visual detection of the results. The lower part 401 accommodated a nitrocellulose test strip 404 on which the anti-VLA-4 antibody 405 was immobilized at a "test site" (T) 406 and a control antibody 407 at a "control site" (C) 408.

Upstream from the test and control sites, there was a fibrous pad ("sample pad") 409 that received the sample 410. Further upstream from the test and control sites there was a "gold pad" 411 of fibrous material where anti-VLA-4 was conjugated to gold particles, the complex being 412. The two-step assay was utilized. In the first step, sample 410 was applied to the sample opening 402 and migrated toward the capture zone 405 ahead of the gold conjugate to form a complex of a sample 410 (anti-anti-VLA4) with the anti-VLA-4 on test line 405. In the second step, the chase buffer 418 was applied to the chase buffer port 417 and rehydrated the anti-VLA-4 gold conjugate 412. The conjugate 412 then traveled toward the capture test line 405 to form a complex with anti-(anti-VLA-4) bound to capture line 405, and the reaction at test site 406 was visualized as a red line 414.

Any excess material, gold, and chase buffer was absorbed at the distal end of the nitrocellulose strip by an absorbent filter pad 416.

The specificity of the test was due to the fact that the complex at the test site only formed when the sample molecule must bind to both the anti-VLA antibody on the test line and anti-VLA-4 gold conjugate. In a simplistic representation, the anti-(anti-VLA-4 antibody) antibody is bridging between the gold labeled anti-VLA-4 antibody and the membrane immobilized anti-VLA-4 antibody, thus, in some cases, this type of assay is referred to as a "bridging assay".

In some embodiments, excess gold-labeled and free anti-VLA-4 antibody can travel further to the control site 408 where a control antibody 407 is available to capture the matrix components, giving rise to an additional visible red line 415.

A reader can be used for semi-quantitative determination of the concentration of the tested analytes. To record the results of the lateral flow system, a reader based on visual positive/negative scoring was used. The visual threshold on the reader corresponds to values within the 20-40 unit range. If the signal was recorded visually positive within this range then it should be considered a very weak pink line that may not be visible to all operators.

Materials

Mouse anti-(anti-VLA-4 antibody) mAB 12C4 (Elan), 2.1 mg/mL

Rabbit anti-(anti-VLA-4 antibody) mAB (Biogen Idec), 1.1 mg/mL

Rat anti-(anti-VLA-4 antibody) mAb 12C2 (Biogen Idec), 1.76 mg/mL

Humanized anti-VLA-4 Ab (Biogen Idec), 21 mg/mL

Humanized anti-VLA-4 Ab formulation buffer (Biogen Idec)

Control antibody

Chase buffer (PBS with 1% w/v BSA and 1% w/v Tween 20)

Gold conjugate (40 nm)

Test Development

A lateral flow immunochromatographic system was developed with the anti-VLA-4 antibody directed against the anti-(anti-VLA-4 antibody) antibody. To determine the appropriate concentration of the capture antibody, anti-VLA-4 antibody was utilized, which was titrated on separate test strips and tested against anti-(anti-VLA-4 antibody) antibody at a range of concentrations from 25 µg/mL to 0.5 µg/mL. The anti-VLA-4 antibody was then immobilized at the test site of the membrane at 0.5 mg/mL. An anti-VLA-4 was conjugated to 40 nm gold particles. The anti-VLA-4 immunogold conjugate was then lyophilized in the conjugate pad and utilized as a detector molecule. At the control site of the membrane, control antibody was utilized.

Results

The 0.5 mg/mL antibody concentration was selected for immobilization based on titration experiments, as it resulted in an intense signal with minimum background. The protocol consisted of adding 20 µL serum (pre-diluted 1:10 in chase buffer or neat) at port 402 immediately (<1 minute) followed by 150 µL chase buffer 418 at port 417. The sample was left to incubate in device for 30 minutes at room temperature and ambient humidity.

The mouse and rabbit anti-(anti-VLA-4 antibody) antibody, humanized anti-VLA-4 antibody, the combination of the above, and the formulation buffer were tested on a flow system with anti-VLA-4 antibody immobilized. The anti-(anti-VLA-4 antibody) antibody was tested at the concentration range of 25 µg/mL to 0.5 µg/mL. The humanized anti-VLA-4 antibody was able to detect the human anti-(anti-VLA-4 antibody) antibody to a concentration of 0.5 µg/mL.

The humanized anti-VLA-4 antibody drug was then used to manufacture test cassettes. FIG. 4 illustrates the specificity of the test utilizing the test cassettes. All tests showed a single band 415, indicating a valid test, but only the cassette for the anti-drug antibody test showed a second band 414, indicating a positive test.

A control line or additional normalization line may be used for the purpose of data normalization in the lateral flow assay. This normalization line may be an immobilized antibody against one of the matrix (e.g., serum) components that have similar concentrations across individual matrix samples. Alternatively, a normalization line may be an immobilized antibody against a protein from an irrelevant species that is not present in the tested matrix, but added at the same concentrations to each matrix sample prior to placing it on a lateral flow device. This protein can be added to each sample directly, or, in case when samples are being diluted with a chase buffer, may be a component of the chase buffer. A reader can be used for semi-quantitative or quantitative measurement of anti anti-VLA4 concentrations.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A device for assaying the level of a humanized anti-VLA-4 IgG4 antibody in a sample from a subject, the device comprising:
   a capture agent associated with a substrate, wherein the capture agent can bind a humanized anti-VLA-4 IgG4 antibody in the sample, and wherein the substrate is a portion of a lateral flow immunochromatographic system comprising, in order of flow, a label zone, a sample receiving zone, and a test zone configured such that:
   the label zone is located upstream of the sample receiving zone and contains one or more secondary agents, the test zone is downstream of the label zone, upon flow through the lateral flow immunochromatographic system the sample reaches the test zone before a secondary agent from the label zone upon flow through the lateral flow immunochromatographic system, and upon flow of the sample through the system, humanized anti-VLA-4 IgG4 antibody from the sample will first bind with a capture agent in the test zone to form a complex, the secondary agent will then reach the test zone, and then the complex will bind with the secondary agent and allow detection of humanized anti-VLA-4 IgG4 antibody; and wherein the capture agent is an antibody or an antigen binding fragment thereof and the secondary agent is an anti-IgG4 antibody or an antigen binding fragment thereof.

2. The device of claim 1, comprising sample.

3. The device of claim 1, comprising sample, and comprising a humanized anti-VLA-4 IgG4 antibody from the sample bound with a capture agent in the test zone to form a complex, wherein the complex does not comprise secondary agent.

4. The device of claim 1, comprising sample, and comprising a complex of a humanized anti-VLA-4 IgG4 antibody from the sample bound with a capture agent in the test zone, and wherein the complex further comprises a secondary agent.

5. The device of claim 1, wherein the binding of the capture agent to the anti-VLA-4 IgG4 antibody produces a detectable signal.

6. The device of claim 1, wherein the device is configured to allow detecting binding of the humanized anti-VLA-4 IgG4 antibody to the capture agent with a secondary agent within the lateral flow immunochromatographic system and determining whether the level of the humanized anti-VLA-4 IgG4 antibody is above or below a predetermined level based on the detecting.

7. The device of claim 6, configured such that the predetermined level is about 1 μg/ml, 2 μg/ml, 3 μg/ml, 4 μg/ml, 5 μg/ml, 6 μg/ml, 7 μg/ml, 8 μg/ml, 9 μg/ml, 10 μg/ml, 15 μg/ml, or 20 μg/ml.

8. The device of claim 1, wherein the sample is blood, plasma, serum, urine, saliva, cerebrospinal fluid, sputum, ocular lens fluid, sweat, milk, ascites fluid, mucous, synovial fluid, peritoneal fluid, transdermal exudates, pharyngeal exudates, bronchoalveolar lavage, tracheal aspirations, semen, cervical mucus, vaginal secretion, urethral secretion, or amniotic fluid.

9. The device of claim 1, wherein the humanized anti-VLA-4 IgG4 antibody is natalizumab.

10. The device of claim 1, wherein the device is configured such that binding of the capture agent to humanized anti-VLA-4 IgG4 antibody is detectable within 30 minutes of the contacting the sample.

11. The device of claim 1, wherein the sample is from a subject that was treated with natalizumab.

12. The device of claim 11, wherein the subject treated with natalizumab has been diagnosed with or is suspected of having a JC virus infection.

13. The device of claim 1, wherein the sample is from a subject that was treated with natalizumab and has been diagnosed with or is suspected of having PML.

14. The device of claim 1, wherein the sample is from a subject that was treated with natalizumab, and wherein the device is configured to allow rapidly monitoring a level of natalizumab in the subject.

15. The device of claim 1, further comprising a control zone downstream from the sample receiving zone.

16. The device of claim 15, wherein the control zone comprises a normalization zone.

17. The device of claim 16, wherein the normalization zone comprises an immobilized antibody against a serum component having similar concentrations across individual samples.

18. The device of claim 16, wherein the normalization zone comprises an immobilized antibody against a protein from an irrelevant species that is not present in blood but which is added at the same concentration to each sample prior to placing the sample in the lateral flow device.

19. The device of claim 18, wherein the protein is added to each sample directly.

20. The device of claim 18, wherein the sample is diluted with a chase buffer comprising the protein.

21. The device of claim 1, wherein the sample comprises a specificity control for assessing specificity of the lateral flow immunochromatographic system.

22. The device of claim 21, wherein the specificity control comprises an agent to which the capture agent and/or secondary agent cross-reacts.

23. The device of claim 22, wherein the agent is an anti-VLA-1 antibody.

24. The device of claim 1, wherein the sample is diluted in buffer.

25. The device of claim 24, wherein the buffer comprises a blocking agent.

26. The device of claim 1, further comprising a chase buffer port for applying chase buffer to the lateral flow immunochromatographic system.

27. A device for assaying the level of a humanized anti-VLA-4 IgG4 antibody in a sample from a subject, the device comprising:
a capture agent associated with a substrate, wherein the capture agent can bind a humanized anti-VLA-4 IgG4 antibody in the sample, and wherein the substrate is a portion of a lateral flow immunochromatographic system comprising, in order of flow, a label zone, a sample receiving zone, and a test zone configured such that:
the label zone is located upstream of the sample receiving zone and contains one or more secondary agents, the test zone is downstream of the label zone, upon flow through the lateral flow immunochromatographic system the sample reaches the test zone before a secondary agent from the label zone upon flow through the lateral flow immunochromatographic system, and upon flow of the sample through the system, humanized anti-VLA-4 IgG4 antibody from the sample will first bind with a capture agent in the test zone to form a complex, the secondary agent will then reach the test zone, and then the complex will bind with the secondary agent and allow detection of humanized anti-VLA-4 IgG4 antibody; and
wherein the capture agent is an antibody or an antigen binding fragment thereof and the secondary agent is an anti-anti-VLA-4 antibody or an antigen binding fragment thereof.

28. The device of claim 27, comprising sample.

29. The device of claim 27, comprising sample, and comprising a humanized anti-VLA-4 IgG4 antibody from the sample bound with a capture agent in the test zone to form a complex, wherein the complex does not comprise secondary agent.

30. The device of claim 27, comprising sample, and comprising a complex of a humanized anti-VLA-4 IgG4 antibody from the sample bound with a capture agent in the test zone, and wherein the complex further comprises a secondary agent.

31. The device of claim 27, wherein the binding of the capture agent to the anti-VLA-4 IgG4 antibody produces a detectable signal.

32. The device of claim 27, wherein the device is configured to allow detecting binding of the humanized anti-VLA-4 IgG4 antibody to the capture agent with a secondary agent within the lateral flow immunochromatographic system and determining whether the level of the humanized anti-VLA-4 IgG4 antibody is above or below a predetermined level based on the detecting.

33. The device of claim 32, wherein the device is configured such that the predetermined level is about 1 µg/ml, 2 µg/ml, 3 µg/ml, 4 µg/ml, 5 µg/ml, 6 µg/ml, 7 µg/ml, 8 µg/ml, 9 µg/ml, 10 µg/ml, 15 µg/ml, or 20 µg/ml.

34. The device of claim 27, wherein the sample is blood, plasma, serum, urine, saliva, cerebrospinal fluid, sputum, ocular lens fluid, sweat, milk, ascites fluid, mucous, synovial fluid, peritoneal fluid, transdermal exudates, pharyngeal exudates, bronchoalveolar lavage, tracheal aspirations, semen, cervical mucus, vaginal secretion, urethral secretion, or amniotic fluid.

35. The device of claim 27, wherein the humanized anti-VLA-4 IgG4 antibody is natalizumab.

36. The device of claim 27, wherein the device is configured such that binding of the capture agent to humanized anti-VLA-4 IgG4 antibody is detectable within 30 minutes of the contacting the sample.

37. The device of claim 27, wherein the sample is from a subject that was treated with natalizumab.

38. The device of claim 37, wherein the subject treated with natalizumab has been diagnosed with or is suspected of having a JC virus infection.

39. The device of claim 27, wherein the sample is from a subject that was treated with natalizumab and has been diagnosed with or is suspected of having PML.

40. The device of claim 27, wherein the sample is from a subject that was treated with natalizumab, and wherein the device is configured to allow rapidly monitoring a level of natalizumab in the subject.

41. The device of claim 27, further comprising, a control zone downstream from the sample receiving zone.

42. The device of claim 41, wherein the control zone comprises a normalization zone.

43. The device of claim 42, wherein the normalization zone comprises an immobilized antibody against a serum component having similar concentrations across individual samples.

44. The device of claim 42, wherein the normalization zone comprises an immobilized antibody against a protein from an irrelevant species that is not present in blood but which is added at the same concentration to each sample prior to placing the sample in the lateral flow device.

45. The device of claim 44, wherein the protein is added to each sample directly.

46. The device of claim 44, wherein the sample is diluted with a chase buffer comprising the protein.

* * * * *